(12) United States Patent
Tsoukalis

(10) Patent No.: US 10,940,261 B2
(45) Date of Patent: Mar. 9, 2021

(54) INFUSION PUMP SYSTEM

(71) Applicant: MICREL Medical Devices S.A., Gerakas (GR)

(72) Inventor: Achilleas Tsoukalis, Anavyssos Attiki (GR)

(73) Assignee: Micrel Medical Devices S.A., Gerakas (GR)

( * ) Notice: Subject to any disclaimer, the term of this patent is extended or adjusted under 35 U.S.C. 154(b) by 572 days.

(21) Appl. No.: 15/485,766

(22) Filed: Apr. 12, 2017

(65) Prior Publication Data

US 2017/0290974 A1 Oct. 12, 2017

(30) Foreign Application Priority Data

Apr. 12, 2016 (EP) .................................. 16164913

(51) Int. Cl.
*A61M 5/142* (2006.01)
*A61M 5/14* (2006.01)
*A61M 39/22* (2006.01)

(52) U.S. Cl.
CPC .......... *A61M 5/142* (2013.01); *A61M 5/1407* (2013.01); *A61M 5/1411* (2013.01);
(Continued)

(58) Field of Classification Search
CPC .. A61M 2005/14208; A61M 2039/229; A61M 2205/18; A61M 2205/3334;
(Continued)

(56) References Cited

U.S. PATENT DOCUMENTS

2003/0233069 A1  12/2003  Gillespie, Jr. et al.
2004/0019464 A1*  1/2004  Martucci ............... H04L 63/126
                                                                              702/189
(Continued)

FOREIGN PATENT DOCUMENTS

EP   2 410 448 A1   1/2012
EP   2881875        6/2015
(Continued)

OTHER PUBLICATIONS

European Search Report from EP App. No. 17166381.8 dated Sep. 20, 2017, 8 pages.

*Primary Examiner* — Brandy S Lee
*Assistant Examiner* — Nidah M Hussain
(74) *Attorney, Agent, or Firm* — Bookoff McAndrews, PLLC

(57) ABSTRACT

An infusion system comprises an infusion pump that comprises an input unit and a display unit. The input unit is adapted for adjusting a value of at least one parameter for controlling operation of the infusion pump and/or an infusion process, and the display unit displays the value of the at least one parameter. The input unit comprises at least one slide bar adapted to be touched by a user's finger and moved along its length to change the value of the parameter, wherein movement in a first direction increases the value of the parameter and in a reversed, second direction decreases the value. The slide bar is adapted so that the rate of change of the parameter value correlates with the speed of the finger movement and in an idle mode is decelerated in a similar way as under influence of an inertia load and/or a friction.

8 Claims, 16 Drawing Sheets

(52) U.S. Cl.
CPC ... *A61M 39/22* (2013.01); *A61M 2005/14208* (2013.01); *A61M 2039/229* (2013.01); *A61M 2205/18* (2013.01); *A61M 2205/3334* (2013.01); *A61M 2205/3379* (2013.01); *A61M 2205/3386* (2013.01); *A61M 2205/502* (2013.01); *A61M 2205/505* (2013.01); *A61M 2205/52* (2013.01); *A61M 2205/6072* (2013.01)

(58) Field of Classification Search
CPC .. A61M 2205/3379; A61M 2205/3386; A61M 2205/502; A61M 2205/505; A61M 2205/52; A61M 2205/6072; A61M 39/22; A61M 5/1407; A61M 5/1411; A61M 5/142

See application file for complete search history.

(56) References Cited

U.S. PATENT DOCUMENTS

| | | |
|---|---|---|
| 2013/0083191 A1 | 4/2013 | Lowery et al. |
| 2013/0144254 A1 | 6/2013 | Amirouche et al. |
| 2014/0012117 A1* | 1/2014 | Mensinger ............. G16H 40/40 600/365 |
| 2014/0276553 A1 | 9/2014 | Rosinko et al. |
| 2015/0151051 A1 | 6/2015 | Tsoukalis |
| 2015/0366945 A1 | 12/2015 | Greene |

FOREIGN PATENT DOCUMENTS

| | | |
|---|---|---|
| EP | 2 987 517 A1 | 2/2016 |
| WO | WO2008019016 | 2/2008 |
| WO | WO2008070054 | 6/2008 |
| WO | WO 2013/043868 A1 | 3/2013 |

\* cited by examiner

FIG. 4
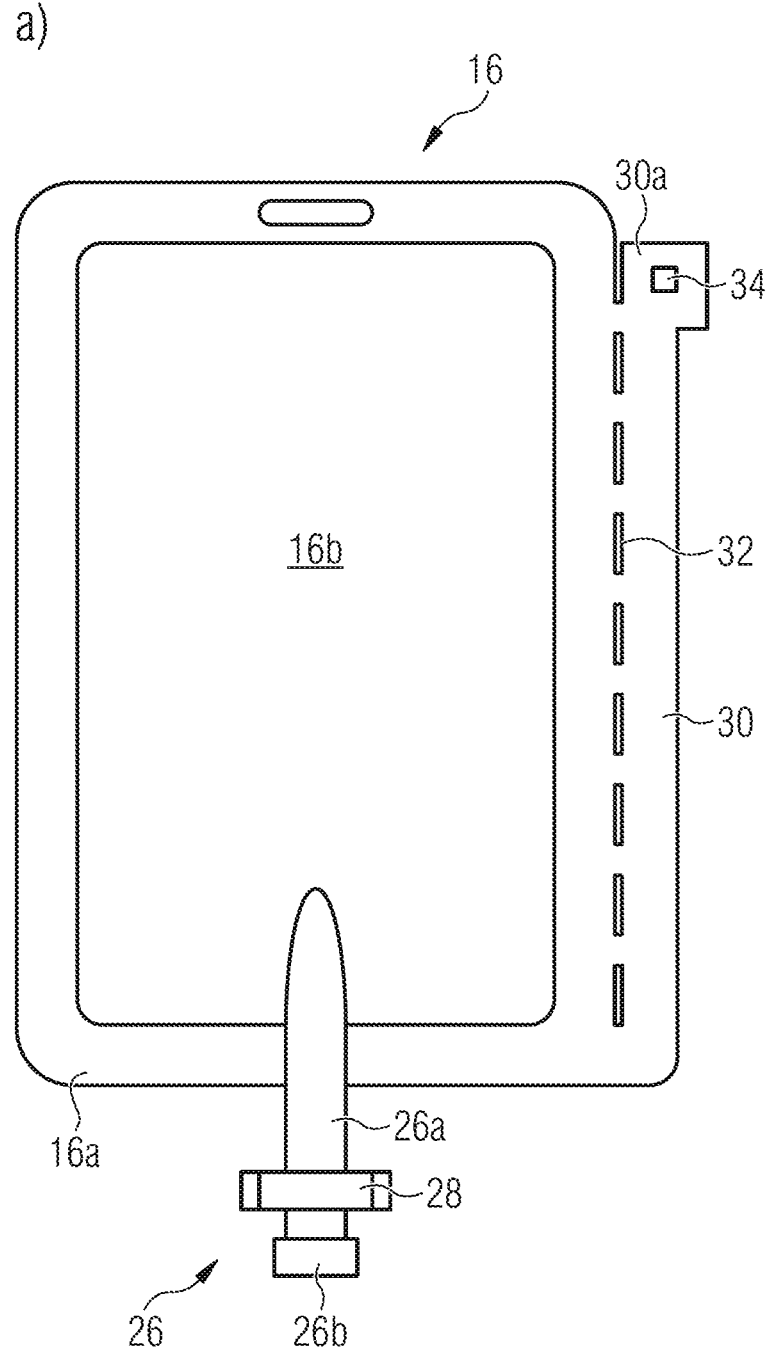
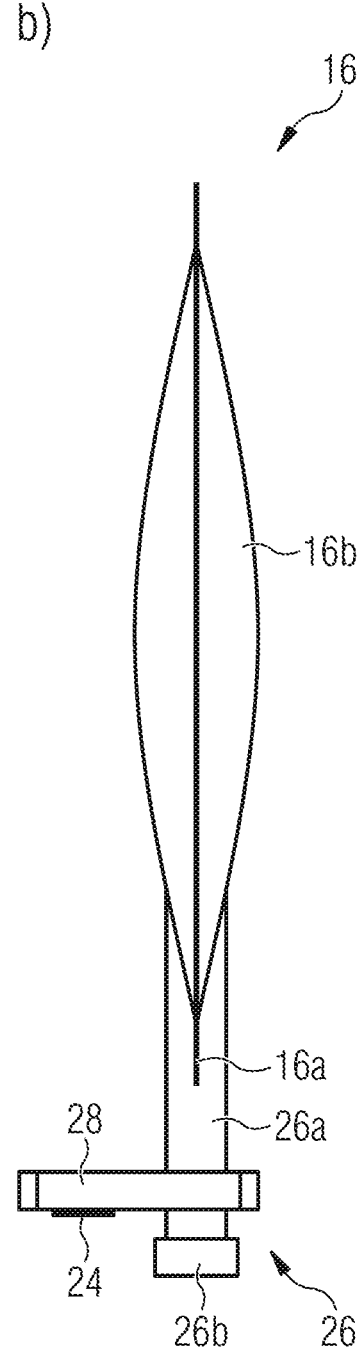

FIG. 5
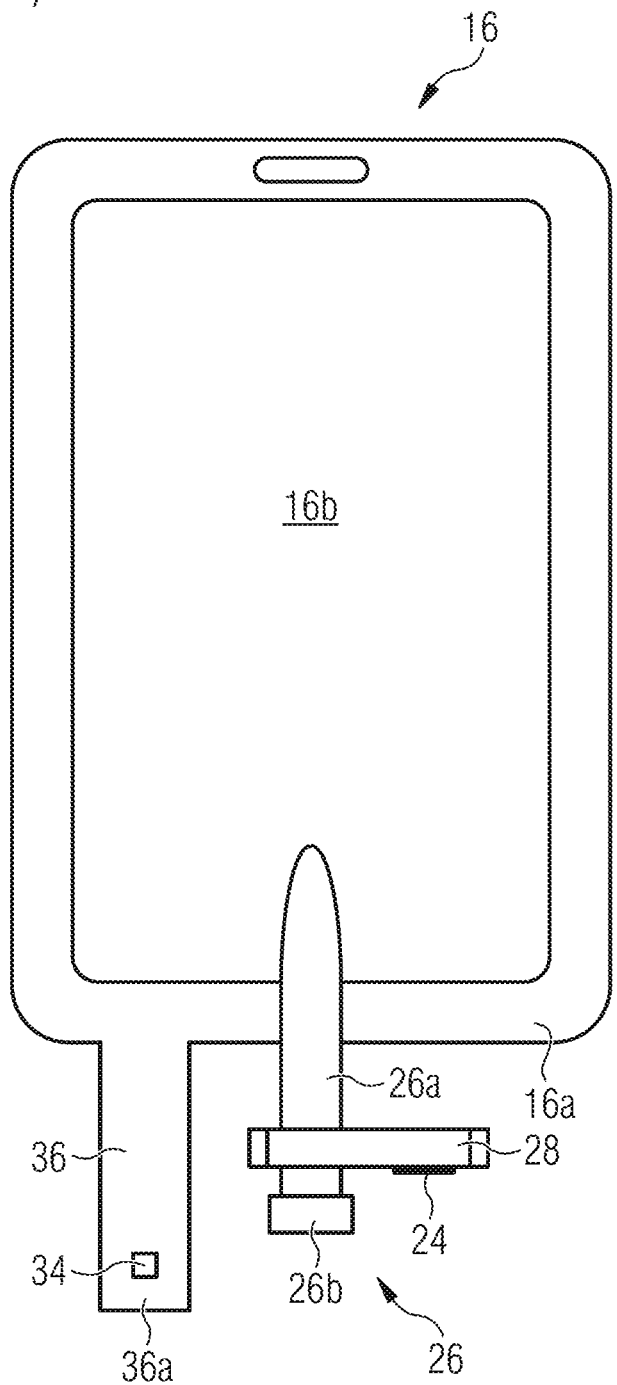
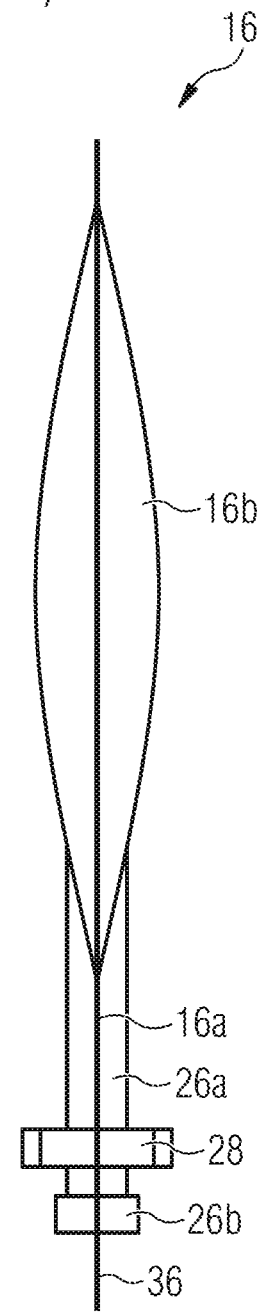

FIG. 6
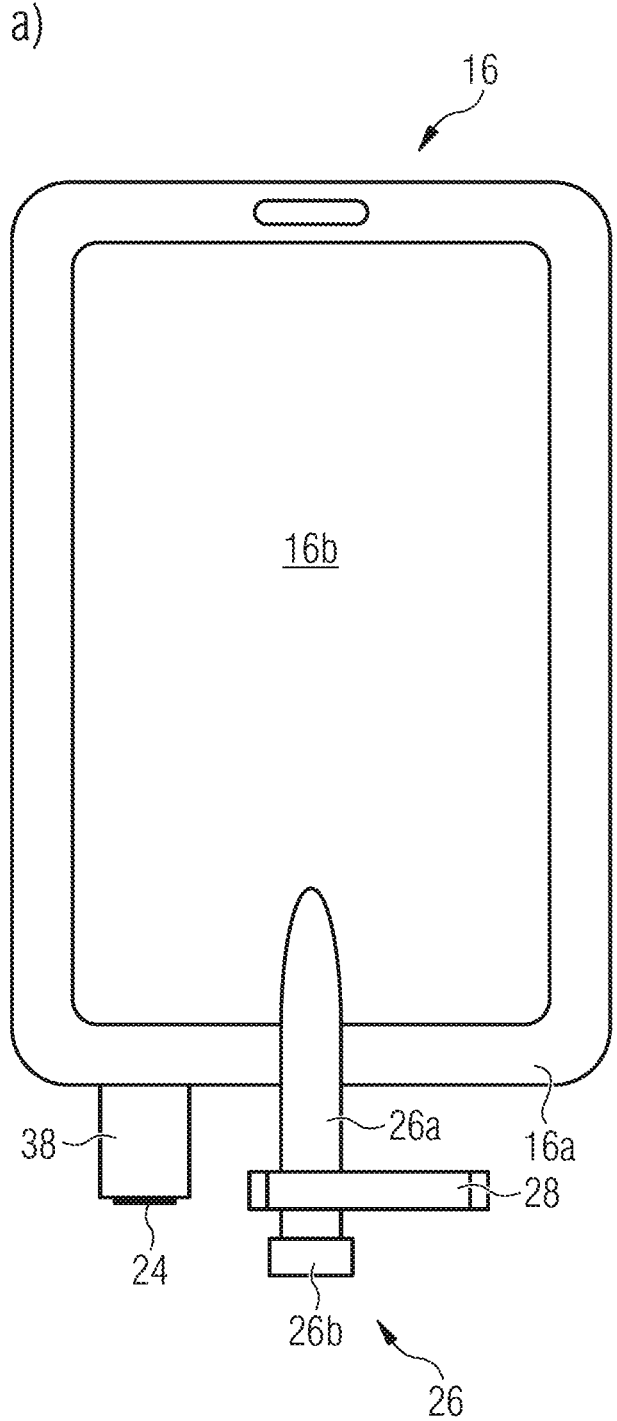
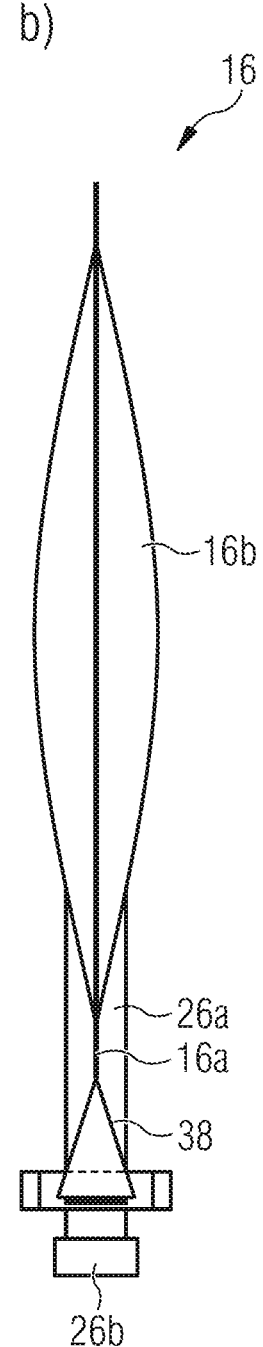

FIG. 7-1
FIG. 7
a)
b)
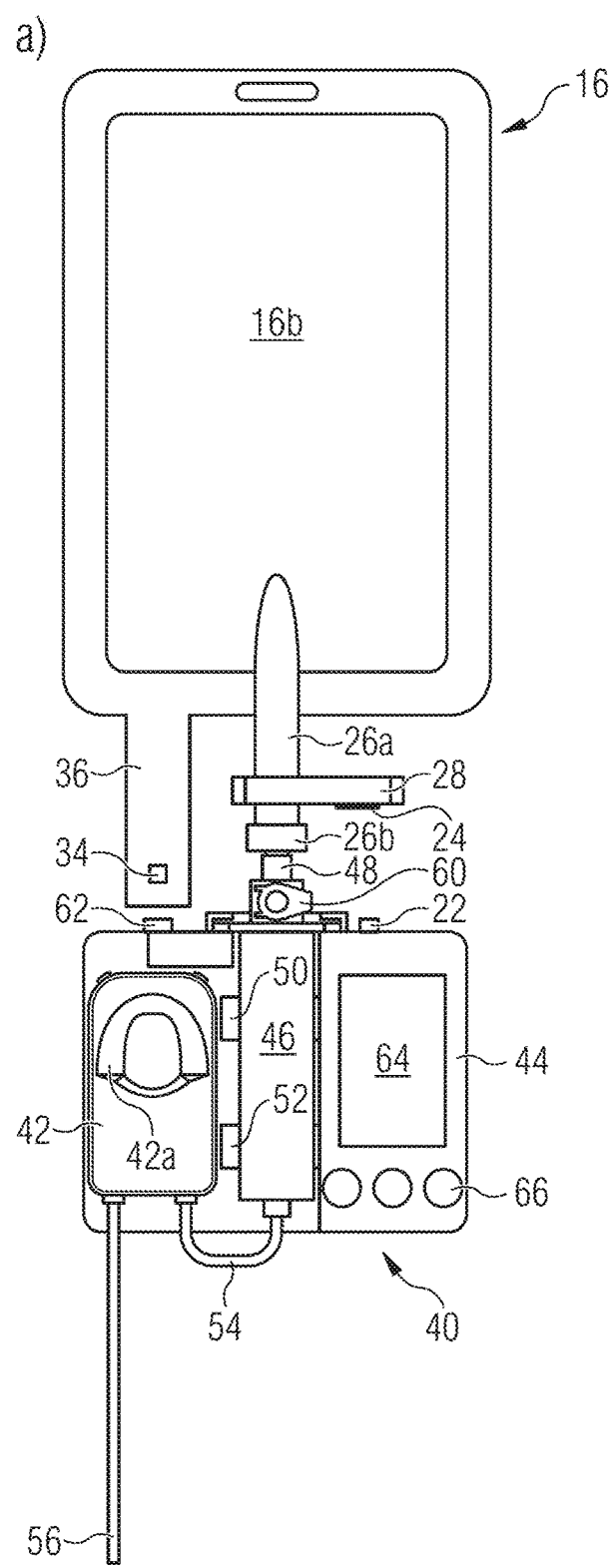
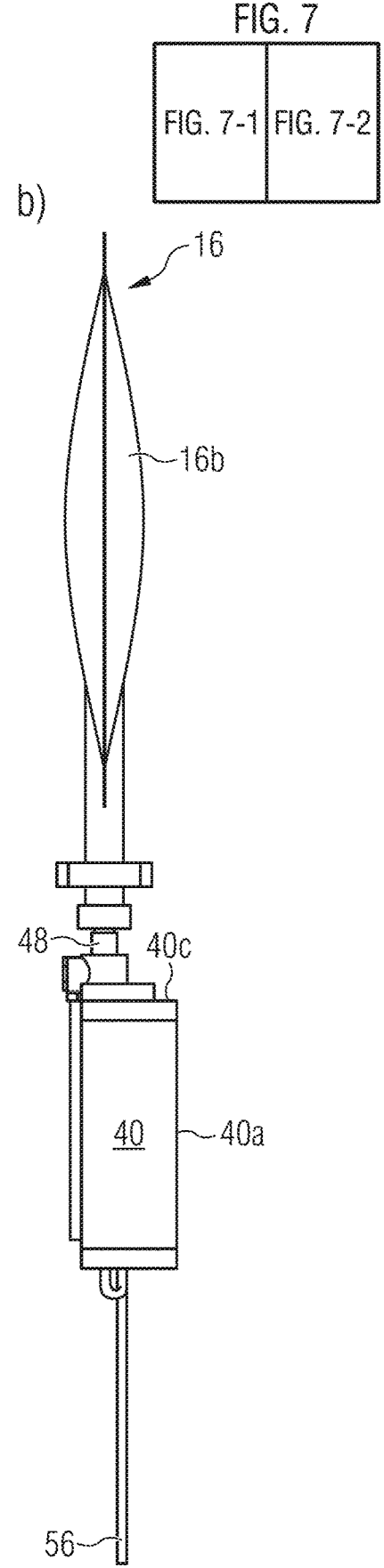

FIG. 8
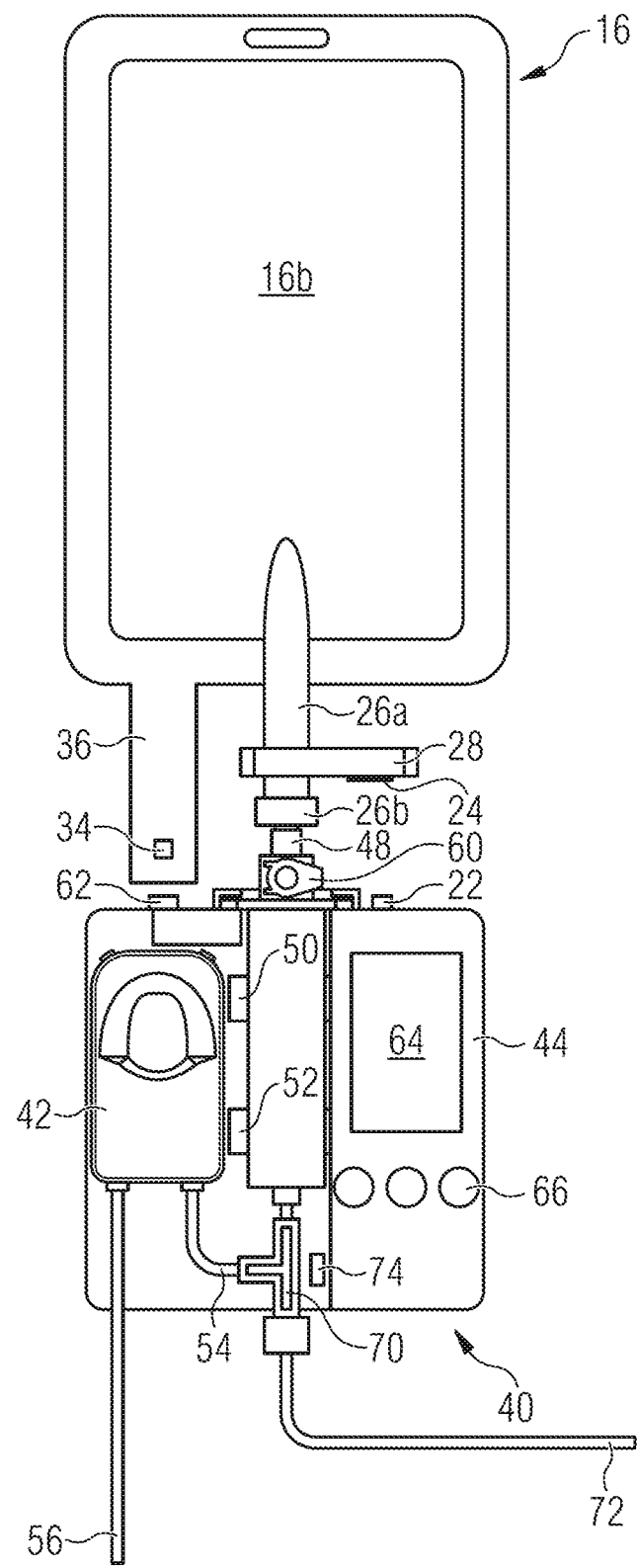
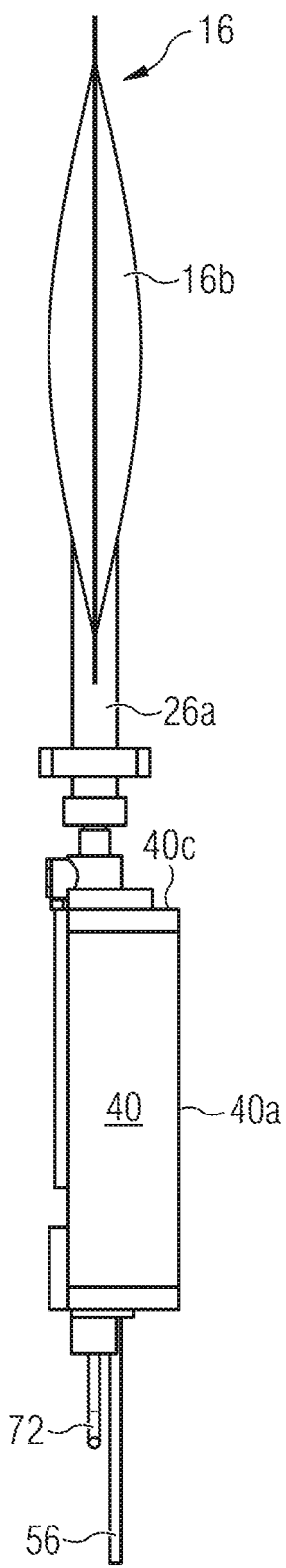

FIG. 9
a) 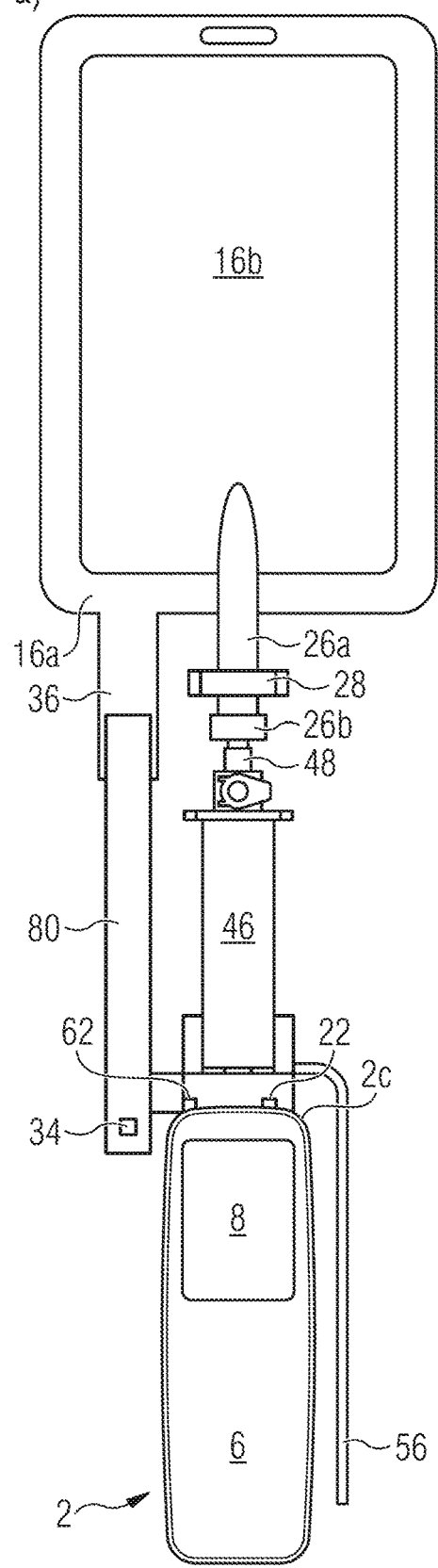   b) 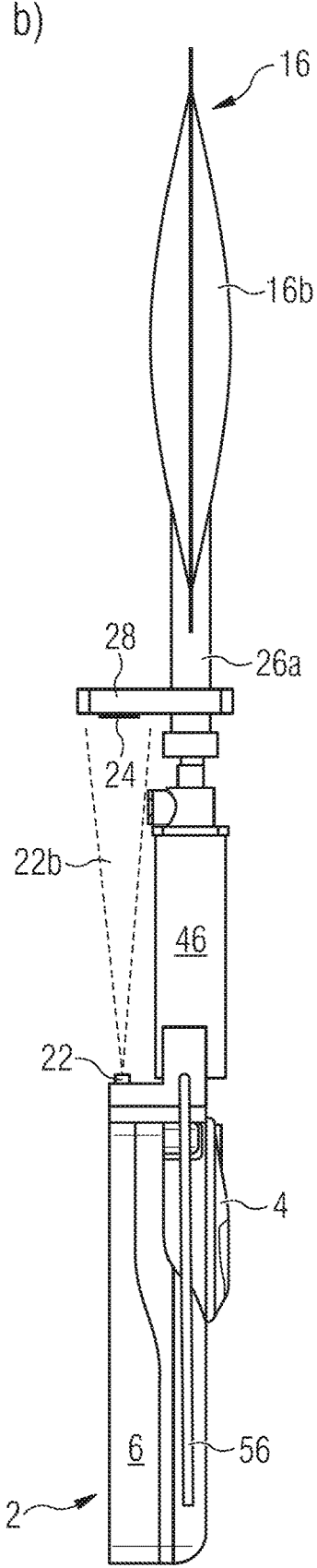

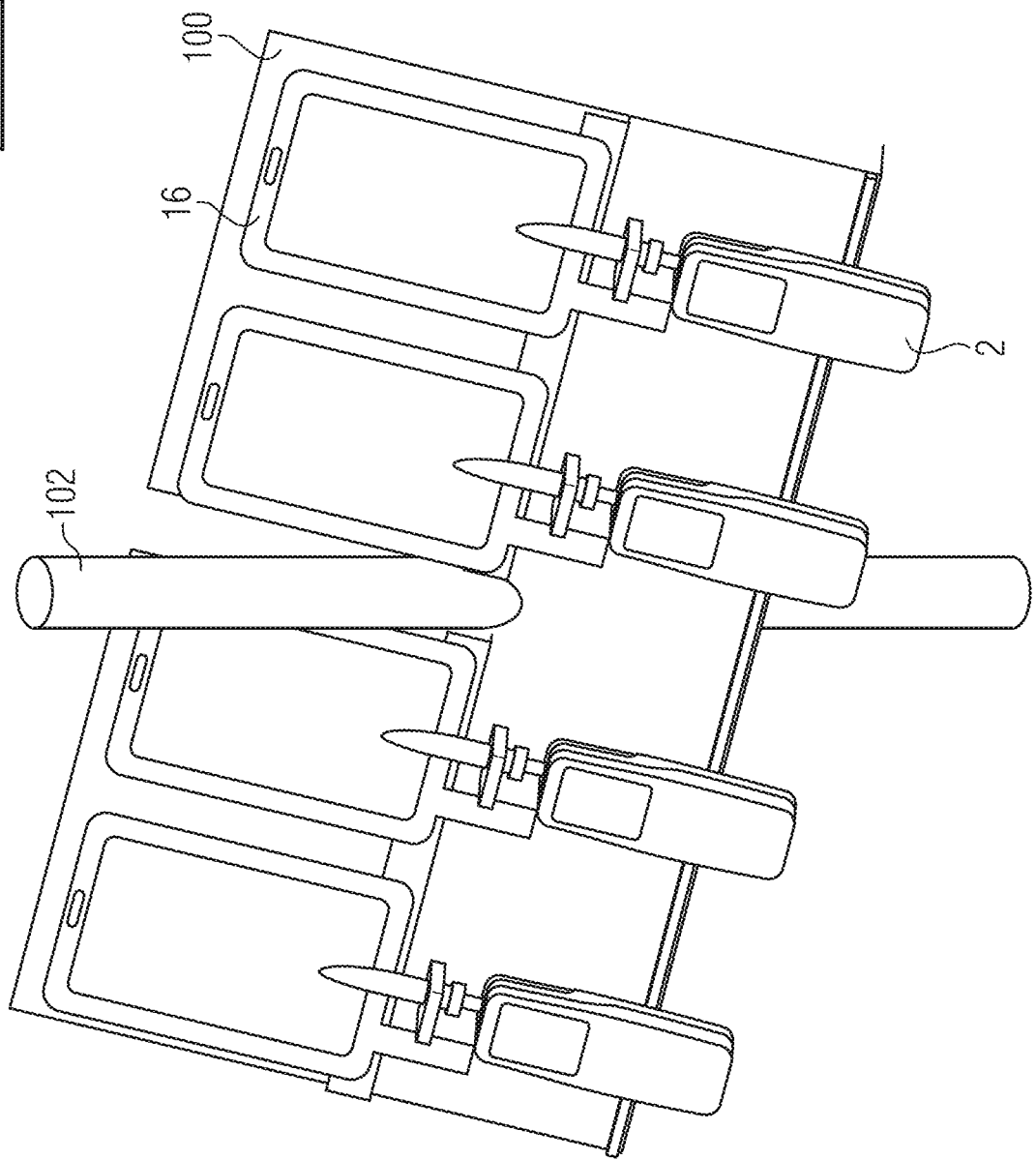

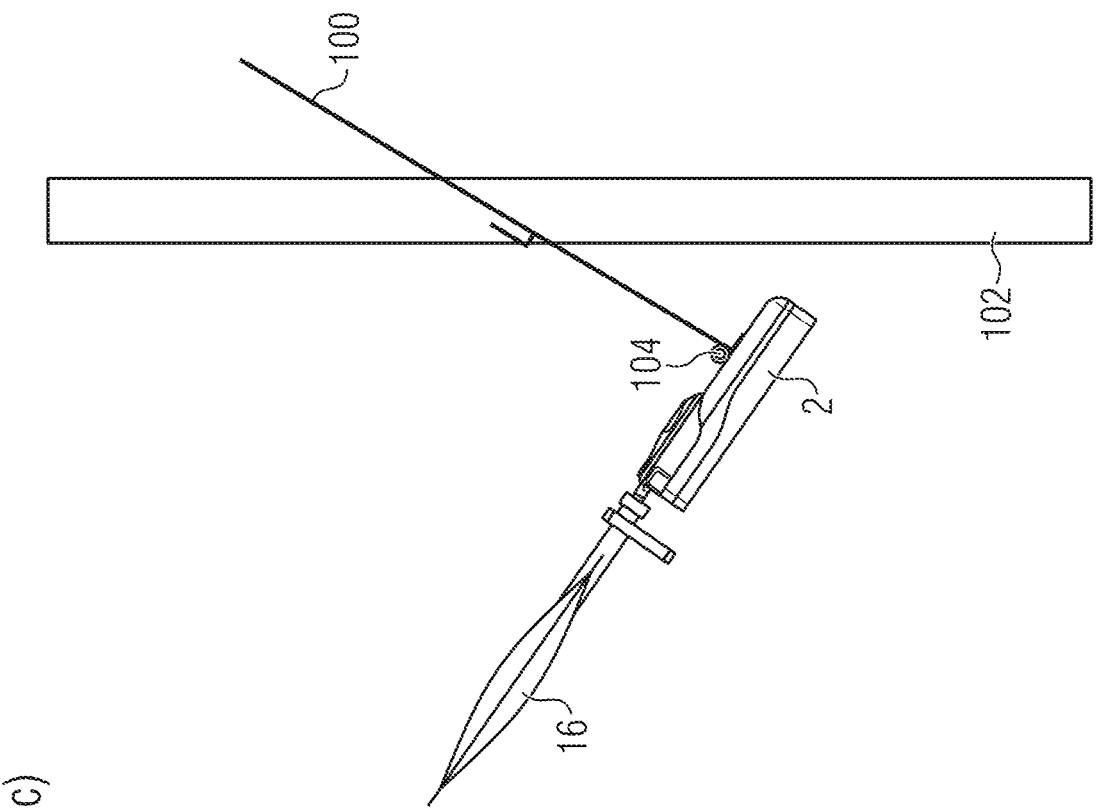
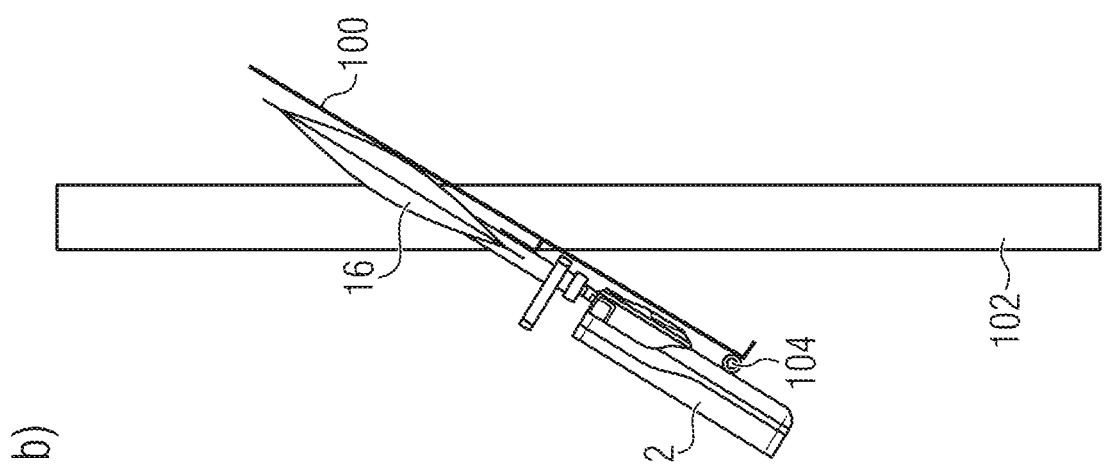

FIG. 14
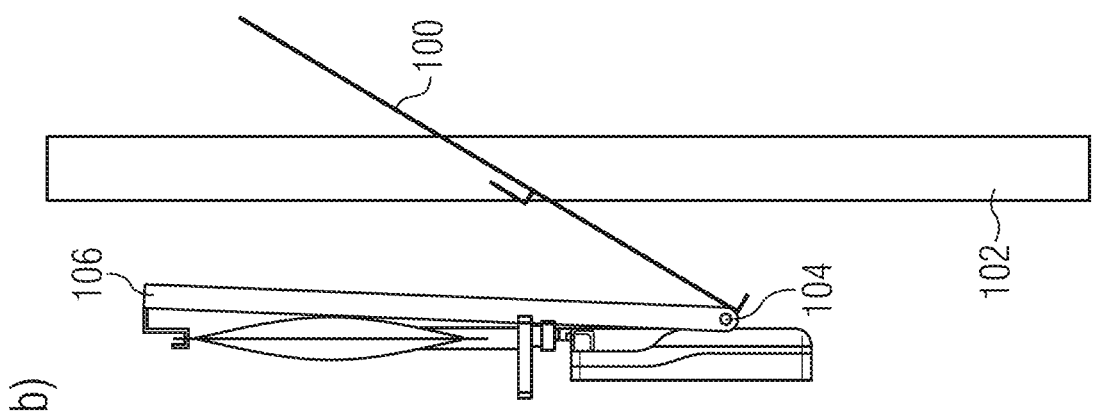
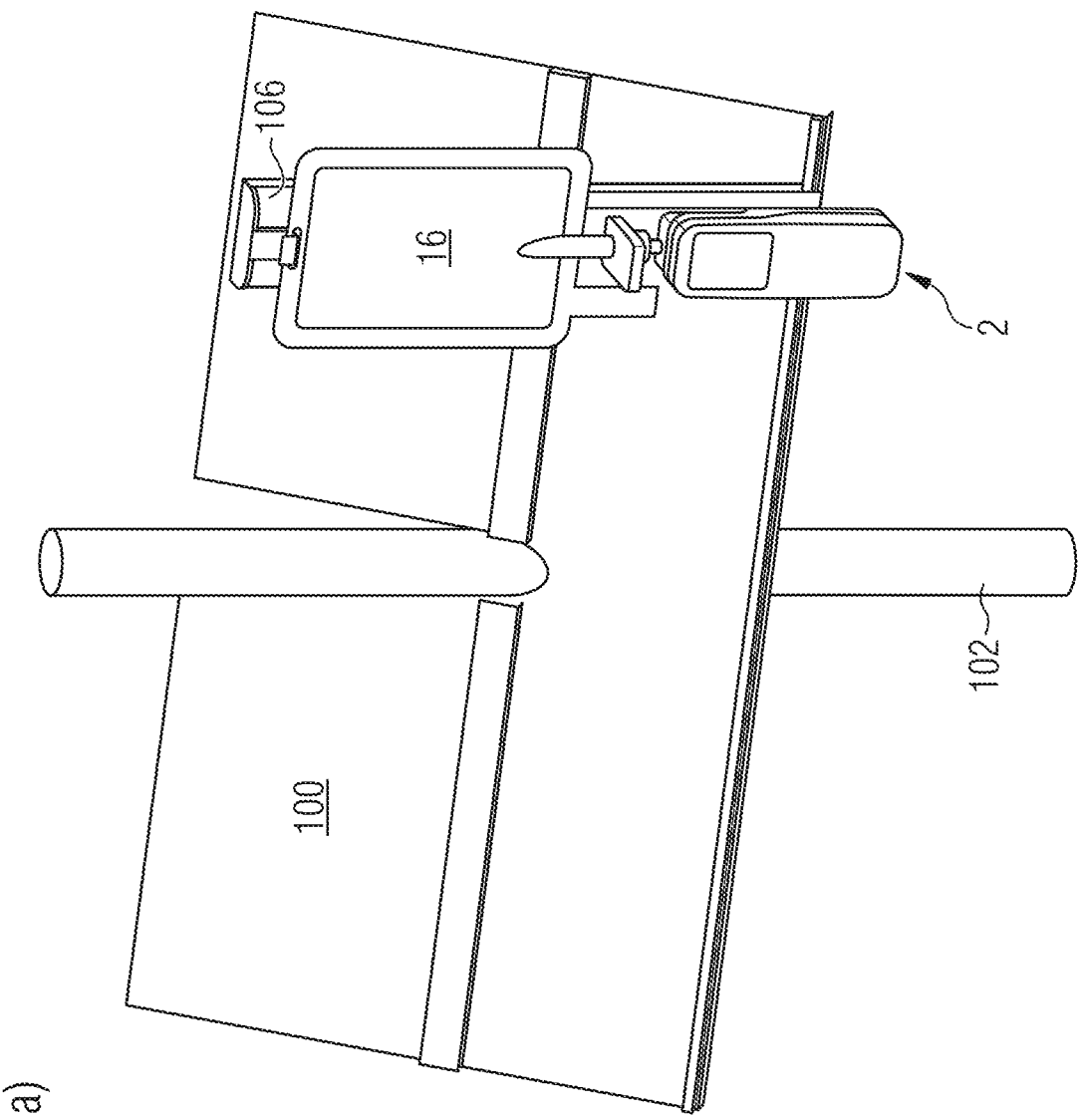

INFUSION PUMP SYSTEM

FIELD OF THE INVENTION

The present invention relates to an infusion system including at least an infusion pump and a medication reservoir connected to the infusion pump.

BACKGROUND OF THE INVENTION

In the prior art, infusion pumps which are provided as so-called large volumetric pumps (LVP) comprise large displays and many button keys for carrying out complex programming and infusion management tasks.

Nowadays, it is still a standard practice in hospitals to use barcodes for labeling drugs and patient identification bracelets instead of RFID/NFC labels which are just beginning to appear mostly on smart identity cards of the medical staff. It is also known in the prior art that with bedside infusion pumps cable-connected barcode readers are used which however have a rather large size.

Despite the use of barcode labeling in conjunction with smart pumps, there is still a risk of upstream line mix-ups when a plurality of infusion pumps are used for one and the same patient. This is in particular the case when a nurse in a hurry situation scans a medication reservoir, then takes an upstream tube and the spike of an infusion set installed in an infusion pump where the scan info is transmitted, and connects to a next medication reservoir instead of the scanned one—a medication error that can eventually cause death since an erroneous drug or medication is infused. As described in the literature, this error is not negligible and causes negative impacts on the smart pump and drug library combination safety solution of the prior art.

SUMMARY OF THE INVENTION

It is an object of the present invention to eliminate the drawbacks of the prior art and in particular to provide an improved infusion system which allows a better and more reliable handling and operation.

In order to achieve the above and further objects, there is provided an infusion system including an infusion pump, said infusion pump comprising an input unit which is adapted for adjusting a value of at least one parameter provided for controlling the operation of the infusion pump and/or an infusion process, and a display unit adapted to display the value of the at least one parameter to be adjusted through the input unit, wherein the input unit comprises at least one slide bar which is adapted to be touched by a user's finger to be moved along its length resulting in a change of the value of the parameter, wherein a movement in a first direction results in an increase of the value of the parameter and in a reversed second direction results in a decrease of the value of the parameter, and wherein the slide bar is adapted so that the rate of change of the value of the parameter essentially correlates with the speed of movement of the finger and in an idle mode is decelerated in a similar way as under influence of an inertia load and/or a friction.

Preferred embodiments and modifications of the present invention are defined in the dependent claims.

According to a preferred embodiment, the input unit comprises several slide bars, wherein each slide bar is provided for a change of the value of a predetermined parameter.

According to a modification of the aforementioned preferred embodiment, the slide bars are arranged in parallel with each other.

According to a further modification of the above preferred embodiment, a first slide bar is provided for adjusting a parameter "volume to be infused" (VTBI), a second slide bar is provided for adjusting a parameter "infusion rate", and a third slide bar is provided for adjusting a parameter "infusion duration", wherein preferably the infusion pump further comprises a calculating unit adapted to calculate, in particular in real-time, one of the three parameters by using the relationship formula infusion duration=volume to be infused/infusion rate with both the other parameters being adjusted through the respective slide bars. Preferably, the display unit comprises a touch screen and the at least one slide bar is provided as a portion of the touch screen.

According to a further preferred embodiment, the input unit comprises a parameter selection unit which is adapted for selecting among several parameters a parameter whose value is to be changed through the slide bar. According to a modification of this embodiment the parameter selection unit is adapted for allocation of one of the several slide bars to one of several parameters, wherein preferably the display unit comprises a touch screen and the selection unit is provided as a portion of the touch screen.

According to a further preferred embodiment, the infusion pump comprises a display screen, and a barcode reader which is adapted to read a barcode provided at a medication reservoir and is arranged so that the reading direction of the barcode reader is oriented away from the display screen at an angle greater than 90° to the plane of the display screen.

According to modification of the aforementioned embodiment, the barcode reader is arranged so that its reading direction is oriented away from the display screen essentially in parallel with the plane of the display screen.

According to a still further modification of the above embodiment, the barcode reader is arranged so that it is positioned above the display screen when the infusion pump is in an operating position so as to ensure a correct orientation of the characters shown on the display screen.

According to a still further modification of the above embodiment, the barcode reader is arranged so that with the infusion pump being connected to a medication reservoir the reading direction of the barcode reader is pointed to a portion of the medication reservoir provided with a barcode.

According to a still further preferred modification of the above embodiment, the infusion pump comprises a first surface portion and a second surface portion, wherein the display screen is provided at the first surface portion and the barcode reader at the second surface portion and wherein the second surface portion is arranged at an angle, preferably about 90°, to the first surface portion, wherein in particular the second surface portion forms an end face.

According to a still further modification of the above embodiment, the infusion pump comprises an inlet port adapted to be coupled directly to an outlet port of a medication reservoir, wherein the barcode reader is arranged so that its reading direction is oriented essentially in direction of coupling the inlet port of the infusion pump with the outlet port of the medication reservoir.

According to a still further modification of the above embodiment, the inlet port is provided at the second surface portion.

According to a still further modification of the above embodiment, the barcode reader is positioned beside the inlet port of the infusion pump.

According to a still further preferred modification of the above embodiment, the infusion pump comprises a first part, preferably a consumable first part, which includes a pump mechanism, and a second part including a motor for driving the pump mechanism of the first part, the first part is reasonably attachable to the second part, the first part is provided with the inlet port, and the second part is provided with the barcode reader.

According to a further preferred embodiment wherein the infusion system includes a medication reservoir, the medication reservoir comprises a reservoir portion for accommodating a medication, and an outlet port which is in fluid communication with the reservoir portion and is arranged below the reservoir portion at a lower edge of the medication reservoir when the medication reservoir is in an operating position, wherein a body is arranged at the lower edge of the reservoir portion and a barcode is provided at a barcode portion of the body facing away from the reservoir portion towards an infusion pump to be connected to the outlet port.

According to a preferred modification of the above embodiment, the barcode portion of the body is essentially arranged in a horizontal orientation with the barcode being provided at the lower side of the barcode portion when the medication reservoir is in an operating position. According to a further preferred embodiment wherein the infusion system includes a medication reservoir, the medication reservoir comprises a reservoir portion for accommodating a medication, and an outlet port which is in fluid communication with the reservoir portion and is adapted to be coupled directly to an infusion pump, wherein a body is arranged at the outlet port and a barcode is provided at a portion of the body facing away from the reservoir portion.

According to a preferred modification of the above embodiment, the body comprises a plate protruding from the outlet port, wherein in particular the outlet port comprises a tube and the plate is arranged at an angle, preferably about 90°, to the longitudinal direction of the tube.

According to a further preferred embodiment wherein the infusion system includes a medication reservoir, the medication reservoir comprises a reservoir portion for accommodating a medication, and a wireless memory provided at a memory supporting element which is attached to the reservoir portion so that in the operating position of the medication reservoir the memory supporting element hangs down from the reservoir portion, wherein the memory supporting element is formed as a flap or tongue.

According to a modification of the above embodiment, the medication reservoir comprises an outlet port which is in fluid communication with the reservoir portion and is adapted to be coupled directly to an infusion pump, and the memory supporting element is positioned at adjacent to the outlet port.

According to a further preferred embodiment wherein the infusion system includes an infusion pump, the infusion pump comprises a wireless memory reading unit adapted to read data through direct wireless connection from a wireless memory provided at a medication reservoir, and a barcode reader adapted to read a barcode also provided at the medication reservoir.

According to a further preferred embodiment wherein the infusion system includes a medication reservoir, the medication reservoir comprises a wireless memory adapted to be read through direct wireless connection by a wireless memory reading unit provided at an infusion pump, and a barcode adapted to be read by a barcode reader also provided at the infusion pump.

Preferably, the wireless memory reading unit and the barcode reader are arranged side by side at the infusion pump at a predetermined distance from each other, and the wireless memory and the barcode are arranged side by side at the medication reservoir at a distance from each other essentially corresponding to the predetermined distance between the wireless memory reading unit and the barcode reader at the infusion pump.

According to a further preferred embodiment wherein the infusion system includes a drip chamber, the drip chamber comprises a chamber portion, an inlet port adapted to be connected to an outlet port of a medication reservoir, a drop collecting portion having an inlet which is in fluid communication with the inlet port and an outlet, a channel having an inlet which is positioned below the drop collecting portion and is in fluid communication with the outlet of the drop collecting portion, and an outlet which is in fluid communication with the interior of the chamber portion, and an outlet port which is in fluid communication with the chamber portion and adapted to be connected to an inlet port of an infusion pump.

According to a modification of the above embodiment, the cross-sectional area of the channel is smaller than the cross-sectional area of the drop collecting portion and/or of the chamber portion.

According to a further modification of the above embodiment, the drop collecting portion has an essentially V-shaped profile.

According to a further modification of the above embodiment, the channel at least partly extends into the chamber portion.

According to a further modification of the above embodiment, the channel is arranged within the chamber portion.

According to a further modification of the above embodiment, the drip chamber comprises two walls, the chamber portion and the channel are provided between both these walls, and the channel is separated from the chamber portion along a contact line where both these walls are sealed with each other, wherein preferably the drip chamber comprises a casing having walls and accommodating at least the chamber portion, the drop collecting portion and the channel and consisting of two halves which along the contact line are sealed with each other, in particular by bonding, so as to separate the channel from the chamber portion, wherein in particular the two halves of the casing are made of semi-soft material, in particular semi-soft plastic.

According to a further preferred embodiment, the infusion system comprises a drip chamber, a drip sensing unit to sense the drip rate of the medication fluid through the drip chamber and a low level detecting unit adapted to detect a predetermined low level of a medication in the drip chamber and to give an alarm in such case.

According to a further preferred embodiment, wherein the infusion system includes an infusion pump, the infusion pump is provided with a cavity adapted to accommodate a drip chamber in a way that the infusion pump can be hanged from the drip chamber.

According to a still further preferred embodiment, the infusion system comprises at least two medication reservoirs each of which has an outlet port, an infusion pump having an inlet port, a stopcock valve having at least two inlet ports each of which is coupled to the outlet port of a different one of the medication reservoirs, and an outlet port which is coupled to the inlet port of the infusion pump, and a stopcock valve position detection unit adapted to detect a current position of the stopcock valve.

The aforementioned and other advantages of the present invention will become apparent from the following more detailed description when taken in conjunction with the accompanying drawings of illustrative embodiments.

BRIEF DESCRIPTION OF THE DRAWINGS

FIG. 4 shows a front view (a) and a side view (b) of a medication reservoir according to a second preferred embodiment;

FIG. 5 shows a front view (a) and a side view (b) of a medication reservoir according to a third preferred embodiment;

FIG. 6 shows a front view (a) and a side view (b) of a medication reservoir according to a fourth preferred embodiment;

FIG. 8 shows a front view (a) and a side view (b) of an arrangement of the medication reservoir according to the third preferred embodiment of FIG. 5 and an infusion pump according to a modification of the second preferred embodiment of FIG. 7 which modification is adapted for use in a piggyback configuration;

FIG. 9 shows a front view (a) and a side view (b) of an arrangement of a medication reservoir according to a modification of the third preferred embodiment of FIG. 5 and an infusion pump according to a second modification of the first embodiment of FIG. 1;

FIG. 13 shows four arrangements of the medication reservoir according to the third preferred embodiment of FIG. 5 and an infusion pump according to the first preferred embodiment of FIG. 1 wherein the arrangements are supported on an inclined rack, in a perspective view (a), a side view (b) and the same side view but with an arrangement of the medication reservoir and the infusion pump being pivoted away from the rack (c) according to a preferred embodiment; and FIG. 14 shows a modification of the embodiment of FIG. 13 in a perspective view (as an example only with one arrangement of medication reservoir and infusion pump) (a) and in a side view (b).

DESCRIPTION OF THE PREFERRED EMBODIMENT

Figure 1:
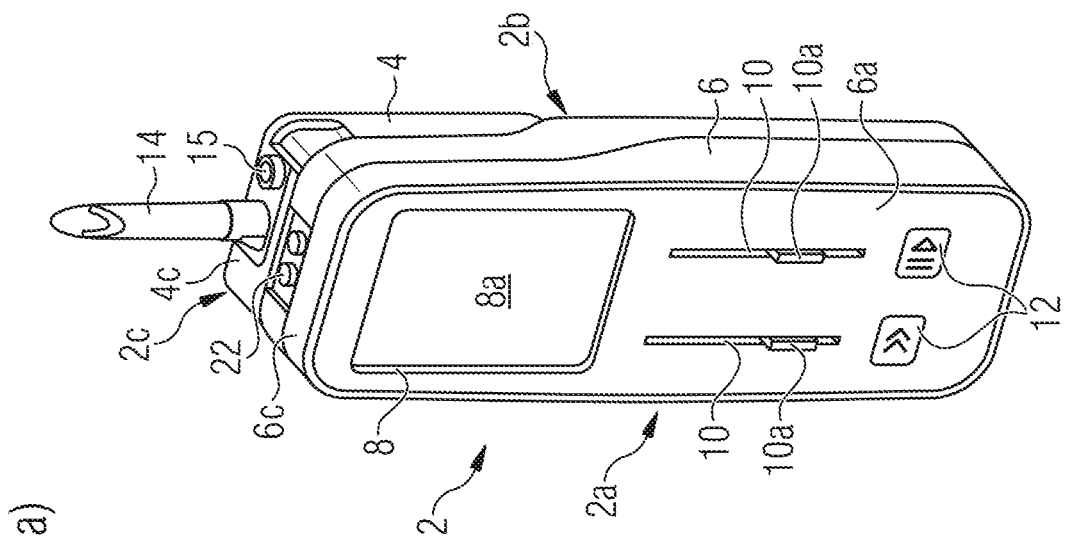
FIG. 1 shows a front side (a) and a back side (b) of an infusion pump according to a first preferred embodiment.
Figure 2:
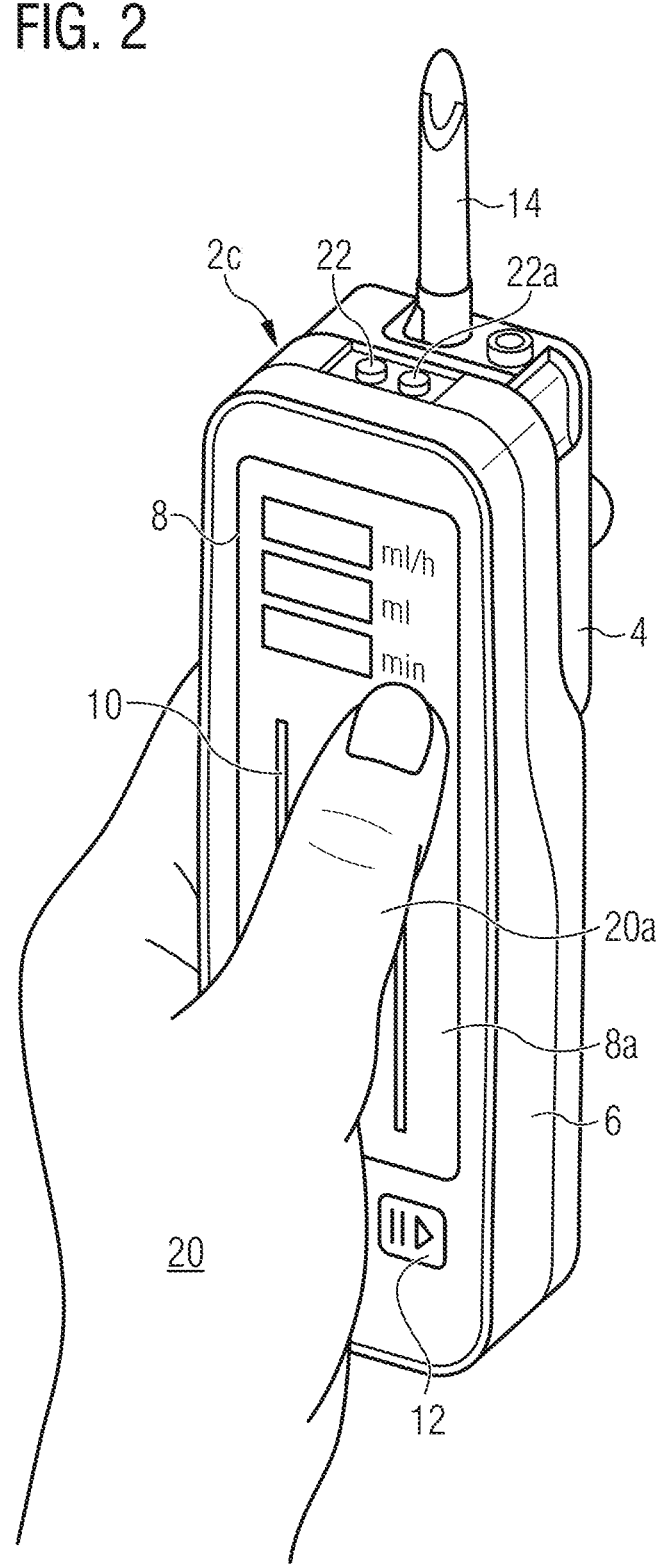
FIG. 2 shows the infusion pump according to a first modification of the first preferred embodiment of FIG. 1 held by a user's hand in an operating condition for adjusting parameters by a user's finger and pointing a barcode reader towards a barcode at a medication reservoir.
Figure 3:
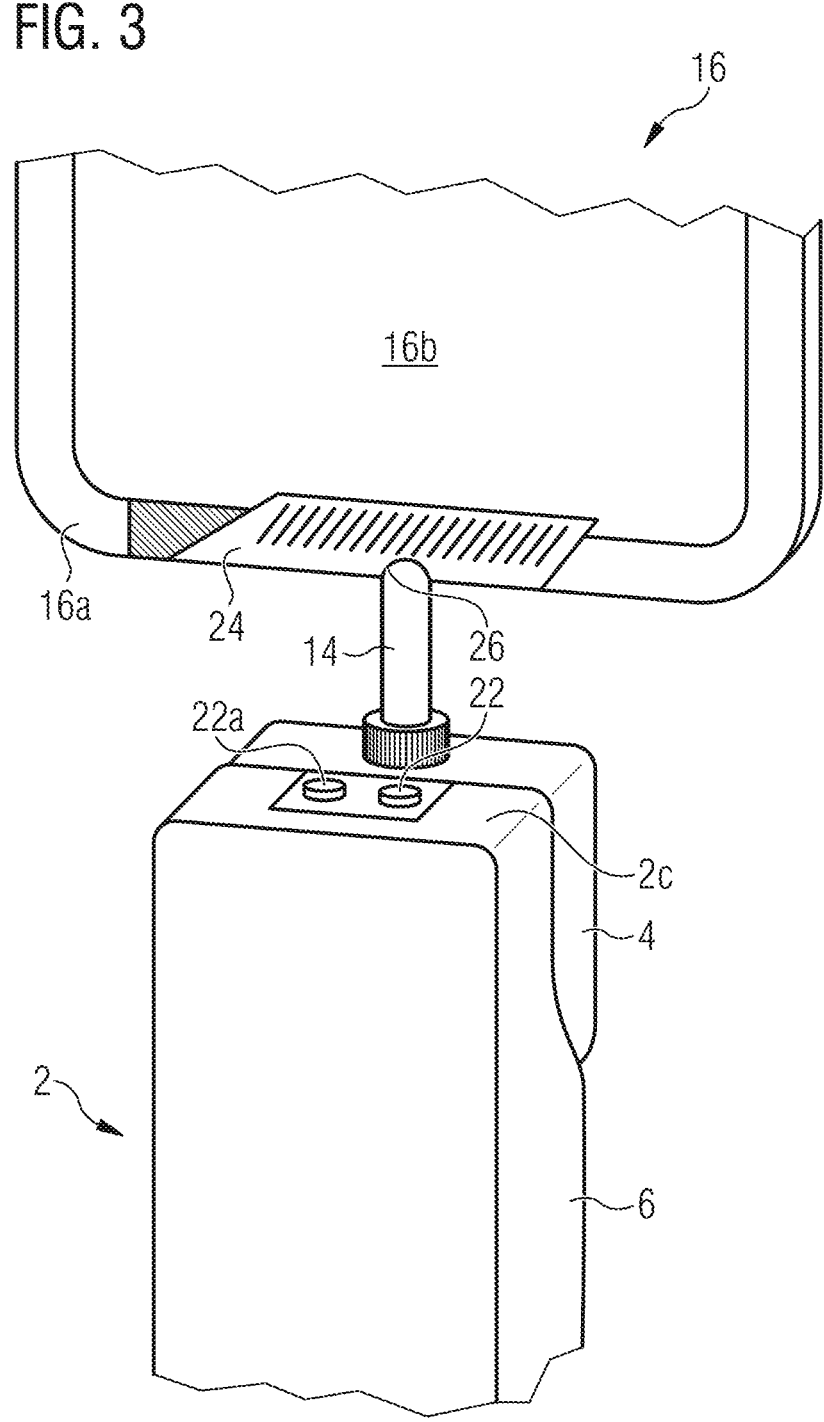
FIG. 3 shows a lower portion of a medication reservoir according to a first preferred embodiment and an upper portion of the back side of the infusion pump of FIG. 1 coupled to the medication reservoir.

In the FIGS. 1 to 3 it is shown an infusion pump 2 according to a first preferred embodiment which configured as a so-called miniature pump and is part of an infusion system. According to the first preferred embodiment, the infusion pump 2 is divided into two parts, i.e. a first part 4 including a pump mechanism (not shown) and a second part 6 including a motor (not shown) for driving the pump mechanism in the first part 4 and further hardware like a display 8 with a display screen 8a, slide bars 10 and buttons 12. According to the embodiment shown in the FIGS. 1 to 3, the first part defines a consumable pump cartridge 4 which is preferably made of plastic resulting in low weight and low manufacturing costs. As further seen from FIGS. 1 to 3, the pump cartridge 4 is provided with a spike 14 which defines an inlet port of the pump mechanism included in the pump cartridge 4 and, hence, of the infusion pump 2, and is further provided with an outlet port 15 to which a downstream infusion line is to be connected. The second part defines the rest of the infusion pump 2 and defines a pump module 6. The pump module 6 which can also be called pump controller has an extremely low weight and a very small size so that it is not bigger than drip sensors of today's bedside pumps and is sufficient to fluidly connect to a medication reservoir 16 a lower portion of which is shown in FIG. 3, resulting in an extreme easiness of use, wherein the medication reservoir 16 is a further part of an infusion system.

As in particular seen from FIG. 1, the pump module 6 is provided so that its front side 6a also defines the front side 2a of the infusion pump 2. The back side 6b of the pump module 6 is provided with a recess 18 for accommodating the pump cartridge 4, as shown in FIG. 1b, so that the back side 4b of the pump cartridge and the remaining free portion of the back side 6b of the pump module 6 together define the back side 2b of the infusion pump 2. The pump cartridge 4 and the pump module 6 are provided with attachment means (not shown) so as to be able to be releasably attached to each other in order to provide the complete infusion pump 2.

As shown in FIGS. 1a and 2, the display 8, the slide bars 10 and the buttons 11, 12 are provided at the front side 6a of the pump module 6 and, hence, at the front side 2a of the infusion pump 2.

In the FIGS. 1 to 3, the infusion pump 2 is shown in an operating condition wherein the infusion pump 2 is held by a user's hand 20 as illustrated in FIG. 2 or coupled to the medication reservoir 16 as illustrated in FIG. 3. In the operating condition, the orientation of the infusion pump 2 is such that one of its side faces defines an upper end face 2c above the display 8, wherein the upper end face 2c of the infusion pump 2 is formed by an upper end face 4c of the pump cartridge and the adjacent upper end face 6c of the pump module 6. Whereas the spike 14 and the outlet port 15a are arranged at the upper end face 4c of the pump cartridge 4, a barcode reader 22 is provided at the upper end face 6c of the pump module 6.

The barcode reader 22, which is adapted to read a barcode provided at a medication reservoir as described later, is arranged so that the reading direction of the barcode reader 22 is oriented away from the display 8 at an angle greater than 90° to the plane of the display screen 8a. According to the preferred embodiment as shown in the FIGS. 1 to 3, the reading direction of the barcode reader 22 is oriented away from the display 8 essentially in parallel with the plane of the display screen 8a so that in the shown embodiment the angle of the reading direction is about 180° to the plane of the display screen 8a and about 90° to the end face 2c of the infusion pump 2; such an orientation of the reading direction of the barcode reader 22 further results in that the end face 2c of the infusion pump 2 is arranged at an angle of about 90° to the front side 2a of the pump which is formed by the front side 6a of the pump module 6. As further to be seen from the FIGS. 1 to 3, the barcode reader 22 is positioned close to the spike 14.

Preferably, a camera based ultra-miniature electro-optical module is provided as a barcode reader 22. Such modules are available with integrated LED light, which is schematically illustrated besides the barcode reader 22 on the upper end face 2c of the infusion pump 2 in the FIGS. 2 and 3, and software for image decoding and hand movement illumination and have the advantage to be integrated in the upper end face 2c of the infusion pump 2 without increasing significantly the small size of the infusion pump 2. It should be added here that the barcode reader 22 can be adapted to read either a one-dimensional barcode or a two-dimensional square-type barcode.

The slide bars 10 each are adapted to be touched by a finger 20a of the user's hand 20 (FIG. 2) which finger when touching the slide bar 10 is moved along the length of the slide bar 10. The slide bars 10 are used to adjust the value of certain parameters wherein the movement of the finger 20a results in a change of the value of the respective parameter. Concretely, the movement in a first direction, which in the operating condition and orientation of the infusion pump 2 according to FIG. 2 is the upwards direction, results in an increase of the value of the parameter and in a reversed second direction, which in the operating condition and orientation of the infusion pump 2 according to FIG. 2 is the downwards direction, results in a decrease of the value of the parameter. Further, the slide bar is adapted so that the rate of change of the value of the parameter essentially correlates with the speed of movement of the finger 20a and in an idle mode, when the user's finger 20a has been released from the slide bar 10, is decelerated in a similar way as under influence of an inertia load and/or a friction. In FIG. 1a, the slide bars 10 each are shown with an operating portion 10a. In case the slide bars 10 are configured as hardware slide bars, the operating portions 10a are sliders of such slide bars. However, in case the slide bars 10 are not hardware slide bars, but provided as a new type of a touch input element without a screen (like a keypad of a notebook), the operating portions 10a define the portion where the finger 20a touches the slide bar 10. Preferably, more than one slide bar 10 is provided. In the embodiment shown, two slide bars 10 are provided which are arranged in parallel with each other. Moreover, in the embodiment shown, the slide bars 10 are arranged so that they extend in an essentially vertical direction when the infusion pump 2 is held in the operating condition and orientation according to FIG. 2.

The buttons 12 are provided for selecting among several parameters a predetermined parameter whose value is to be changed through a predetermined one of the slide bars 10, wherein one of the buttons 12 is allocated to one of the slide bars 10—except when e.g. three slide bars can adjust two parameters simultaneously.

FIG. 2 shows a modification which differs from the embodiment as shown in FIG. 1a in that the display screen 8a is embodied as a touch screen wherein the slide bars 10 are provided as a portion of the touch screen. Although in FIG. 2 the buttons 12 are provided as hardware buttons and arranged below the display 8, alternatively they can also be provided as a further portion of the touch screen. According to the embodiment shown in the figures, the infusion pump 2 has an elongated shape. Due its small size and its elongated shape, the infusion pump 2 can be held by the user's hand 20 somewhat like a TV remote control and can further be programmed by a single finger 20a of the user, as also illustrated in FIG. 2, so as to achieve a single hand handling and finger programming as well as scanning labels at medication reservoirs or patient bracelets by means of label readers like the barcode reader 22 provided at the upper end face 2c. Accordingly the infusion pump 2 is also used as a normal barcode reader of the prior art for scanning patient ID and drug labels by moving the infusion pump 2 towards and pointing the label by hand. The infusion pump 2 beeps when a reading is available, as bar code readers do, and shows on the display 8 the reading as part of a "5R" ("right patient", "right drug", "right dosing", "right delivery route", "right time") check and setup.

In the infusion pump 2 usually a downloaded drug library is stored so that it can associate a drug name and eventually concentration and volume to a scanned label in case there is a hand written or printed prescription. Since electronics and memories nowadays are extremely small, a big size infusion pump is not needed anymore to integrate big software. The infusion pump 2 according to the described embodiment also having Wi-Fi communication and being interoperable by interoperability standards can download a prescription having all "5R" doctors' recommendations for a specific patient.

After scanning a patient and scanning the drug or medication reservoir, this information can be transferred through Wi-Fi to an e-prescription server (not shown) so to send all rest "5R" information, i.e. infusion protocol, delivery route (intravenous or other), and time to start infusion. All this information is then displayed at the display 8 of the infusion pump 2 and checked by a nurse responsible for the infusion management. The process also eases the programming on the infusion pump 2 since patient attributes like age and weight and Body surface Area (BSA) are downloaded and used in drug library limits and dose (ml/Kg/min) calculation. Alternatively, only patient related drugs pending, not yet infused from a drug/pharmacy automation hospital system are shown on the infusion pump 2 since drug and patient are identified.

The display 8 of the infusion pump 2 according to a preferred embodiment is intentionally black and white to significantly reduce power consumption that nowadays is much higher. Whereas a touch screen is unusual to black and white displays, a touch screen display has not much power consumption so that it can be used for the usability it offers.

The touch screen of the display 8 for the usability increase provided in infusion pump programming is advantageous for rate calculation and other letter or number selection functions. The slide bar 10 that the user's finger 20a (FIG. 2) slips over it and the display 8 shows a changing number with speed relative to speed of the finger 20a and its acceleration. As already mentioned above, this function mathematically is that of an inertia wheel with some friction: You accelerate it and it continues while decelerating if no more "push" from the finger 20a. When the finger 20a stops on the display 8, the value of the parameter indicated as a number resumes and changes direction if the finger 20a changes so. This is much easier than up/down buttons used in prior art and much more appropriate for the use of the infusion pump 2 somewhat like a TV remote control, where slipping a finger is a much natural function. It can be adapted to a large dynamic range of e.g. 0.01 to 1500.00 ml/h rate for speed and easiness of adjustment. A preferred embodiment would have numbers on top and touch-slip-bars at the lower end of the display 8.

Especially for rate programming, there are three variables related by an equation involved in rate programming (the simplest infusion protocol) RATE=VOLUME/TIME.

Since gravity infusions are by far the largest market segment in infusion, delivering just by rate programming and the form and function of the infusion pump 2 can also replace gravity infusions, it is provided the simplest user interface to program a rate as follows. Alternatively, three slide bars 10 can be used with allowance to simultaneously change only two from the three parameters and adjust all three parameters in real time with the aid of the display 8.

SIMPLE INFUSION screen

With just two touch-slide bars used, three numbers change calculated real-time. The first represents VOLUME TO BE INFUSED and the second RATE Display:

VTBI XXX.XX ml

RATE XXX.XX ml/h UNITS

TIME XXX.XX h.min OPTIONS

Touch-"Slide"-Bars

VTBI RATE

While two slide bars 10 are operated, the values of the aforementioned three parameters shown on the display 8 change after continuous calculation: VTBI as slide bar input, RATE as slide bar input, and TIME=VTBI/RATE. So Volume & Rate or Volume & Time protocols can be programmed with one single display screen 8a.

An OPTIONS touch button for time are hours/min or min only. A UNITS touch button if not pressed slides go to ml/h as RATE XXX.XX ml/h UNITS so that you can still change if UNITS pressed between "ml/h", "mg/h", "mcg/h" and "mg/Kg/min". Both these aforementioned touch buttons are not shown in the figures, but can be additionally provided as further parts of the touch screen according to the modified embodiment of FIG. 2. In case of "mg" or "mcg", CONCENTRATION is needed. Concentration if read by drug label needs no entry; if not, a slide bar 10 can be used for entering it before programming rate.

In case of mg/Kg/min, Kg of patient is needed. This is also entered by a slide bar 10.

First display options: It appears after a cartridge 4 is mounted on the infusion pump 2 since there is preferably no ON/OFF button. The infusion pump 2 shuts OFF display and keeps location tracking to find its position after it is on standby, and cartridge 4 is removed and no touch on buttons or touch screen is done for some time.

1. RESUME/REPEAT INFUSION
2. NEW PATIENT
3. DRUG LIBRARY
4. NEW PROGRAM/MODE
5. CONFIGURATION and two slide bars 10 below for Volume and Rate.

If touched, then a gravity type SIMPLE INFUSION screen is shown, by using two slide bars 10 for programming new infusion as shown above. This is an easy way of doing complex things as below, while going directly to program infusions like gravity replacements:

1. "RESUME/REPEAT INFUSION" continues an interrupted infusion. It also repeats last infusion as same VTBI is also proposed after an infusion has previously alarmed END of Infusion. This function eases Home Care infusions that for chronic patients are much the same.

For further facilitating home care infusions, a touch button "PROTOCOLS" appears, to show most used protocols and select one from those.

2. "NEW PATIENT" menu can be replaced by patient scan. If patient ID label is not available, a slide bar 10 shows all letters from A-Z to program a new patient name.

A bar code or RFID is used to scan patient or drug, and NEW PATIENT entry on the infusion pump 2 is sent to a drug library option

3. DRUG LIBRARY

Screen parameters can be entered by scanning barcode or RFID or WiFi transfer or slide in letters all alphabet from A-Z scrolls from slider 3.1 CARE AREA as above or slide in from a hospital list due to a selection or it can also be retrieved from a geolocation function of a server receiving Wi-Fi signal strengths sensed by the infusion pump, and comparing them to predefined locations in an adaptive system described in EP2881875A2 or US20150151051A1. From care area the correct drug library is checked that is in the infusion pump 2 or downloaded. The drug library contains limits for each drug and patient attributes as known in the art.

3.2 PATIENT NAME as above or from hospital from care area list of patients 3.3 DRUG NAME as above or from hospital drug list for patient 3.4 CONCENTRATION as above After all this is defined, the infusion pump 2 retrieves from a server (not shown here) the rest of 5R as delivery route and time to infusion and the protocol for infusion, and a nurse checks them on the infusion pump 2, and then she can start infusion safely.

4. NEW PROGRAM/MODE

This menu shows 4.1 RAMPS (shows Ramp programming mode)

4.2 INTERMITTENT (shows intermittent programming mode)

4.3 PCA/BOLUS (shows PCA with bolus parameters programming mode)

4.4 RATE (shows rate programming as SIMPLE INFUSION above)

5. CONFIGURATION

This menu adjusts all infusion pump configuration parameters one by one.

For medication safety, scanning a barcode of a drug or a medication reservoir that is few centimeters above the infusion pump that is hanging from its spike is not 100% safe but nevertheless much better than conventional infusion pumps with an upstream tubing that scan a drug reservoir a meter higher. Namely, scanning the wrong medication reservoir is reported as medication error happening many times. According to a preferred embodiment of the arrangement as shown in FIG. 3, it is provided a 100% safety.

There is a barcode label 24 on the lower border or edge 16a of the reservoir portion 16b being part of the medication reservoir 16 so that the barcode label 24 is provided as somewhat like a continuation of the lower border or edge 16a of the medication reservoir 16, as shown in FIG. 3. Since the barcode reader 22 is positioned above the display 8 and arranged on the upper end face 2c of the infusion pump 2, when the infusion pump 2 is in an operating position according to the FIGS. 2 and 3 so as to ensure a correct orientation of the characters shown on the display screen 8a of the display 8, the reading direction of the barcode reader 22 is pointed to the barcode label 24 at the lower border or edge 16a of the medication reservoir 16, when the medication reservoir 16 is also in an operating position according to FIG. 3, after the spike 14 of the infusion pump 2 has been directly connected to an outlet port 26 of the medication reservoir 16. As further shown in FIG. 3, the barcode label 24 is positioned close or adjacent to the outlet port 26 at the lower border or edge 16a of the medication reservoir 16 so that in the shown embodiment the reading direction of the barcode reader 22 is oriented essentially in direction of coupling the spike 14 of the infusion pump 2 with the outlet port 26 of the medication reservoir 16. So, due to the aforementioned configuration it is ensured to allow an appropriate distance between the barcode reader 22 and the barcode label 24 for correct reading, wherein it is also possible to adjust such a distance by the provisions of spacers at the infusion pump 2 and/or the barcode label 24.

For piggyback infusions and conventional infusion pumps having an upstream tubing, a combination of a flow sensor or an active pinch valve or both with a barcode reader configured for a close-up label as described above and facing the barcode label at a specific distance can also achieve a 100% medication safety as the infusion pump senses in one case the flow at start of infusion needing flow increasing from 0 and in another case with an upstream pressure reading at starting the infusion, when an active valve is closed, the upstream pressure is decreasing.

The barcode labels of the kind as described above can be printed by a special printer that reads the barcode of a drug and prints a copy on a self-adhesive label that is attached to the lower border or edge 16a of the medication reservoir 16 aside the outlet port 26 of the medication reservoir 16. Instead of the configuration shown in FIG. 3, an L-shaped flap or plate (not shown) can be attached to the lower border or edge 16a of the medication reservoir 16, in particular by bonding, wherein the barcode label is provided at the lower side of the vertical portion of the L-shaped flap or plate protruding from the medication reservoir so that the barcode label faces the barcode reader 22 at the top or upper end face 2c of the infusion pump. According to a further modification (also not shown) instead of the configuration shown in FIG. 3, the barcode label can be bonded to the lower border or edge 16a of the medication reservoir 16 so as to get the shape of an "L" below the lower border or edge 16a of the medication reservoir 16.

FIG. 4 shows a second preferred embodiment of the medication reservoir 16 which differs from the first preferred embodiment of FIG. 3 in that the outlet port 26 comprises a short tube 26a which is in fluid communication with the reservoir portion 16b and extends or suspends downwards when the medication reservoir 16 is in an operating position as shown in FIG. 4. The lower free end of the tube 26 is formed as a connector 26b which is adapted to be directly coupled with an infusion set including a drip chamber and an infusion pump wherein the drip chamber can be preferably provided with an upstream connector (not shown). Attached to the wall of the tube 26a of the outlet port 26 is a plate 28 which protrudes from the outlet port 26 at an angle of about 90° and, with the medication reservoir 16 being in its operating position, in an essentially horizontal direction as shown in FIG. 4b. The lower side of the plate 28 facing away from the medication reservoir towards the aforementioned infusion set is provided with a barcode label 24. As further shown in FIG. 4a, the medication reservoir 16 according to the second preferred embodiment comprises a strip 30 which is integral with the reservoir portion 16b at its lower edge 16a but separated from the remaining part of the reservoir portion 16b by a perforated line 32. So, the strip 30 is provided as a side detachable strip 16 which by rupturing the perforated line 32 can fold downwards wherein its end 30a will be lower than the level of the lower edge or border 16a of the reservoir portion 16b. The end 30a of the side detachable strip 30 is provided with a wireless memory which in the described embodiment is configured as a RFID/NFC label or chip 34. With the side detachable strip 30 being folded downwards the RFID/NFC label 34 at the end 30a of the side detachable strip 30 is positioned within an appropriate distance to a RFID/NFC reader provided on an infusion pump to be described later.

FIG. 5 shows the medication reservoir 16 according to a third preferred embodiment which differs from the second preferred embodiment of FIG. 4 in that instead of a side detachable strip 30 there is provided a tongue or flap 36 which is attached to the lower edge 16a of the reservoir portion 16b and suspends or extends downwards when the medication device 16 is in its operating position as shown. The flap or tongue 36 is provided at its lower free end 26a with the RFID/NFC label 34.

FIG. 6 shows a fourth preferred embodiment of the medication reservoir 16 which differs from the aforementioned second and third preferred embodiments in that the barcode label 24 is not provided at the plate 28 attached to the tube 26a of the outlet port 26, but at the underside or bottom of a body 38 attached to the lower edge 16a of the medication reservoir 16 and suspending downwards therefrom wherein the body 38 is embodied as a plate or flap which is folded to a triangle whose peak is fastened to the lower edge 16a of the reservoir portion 16b and whose bottom extends in an essentially horizontal direction when the medication reservoir is in its operating position as shown in FIG. 6b. So, in contrast to the second and third preferred embodiments, in the fourth preferred embodiment of FIG. 6 the plate 28 can be provided for supporting an RFID/NFC label.

All the above described second to fourth preferred embodiments of the medication reservoir 16 show a combined use of a barcode and a wireless memory like an RFID/NFC label or chip. Accordingly, the infusion pumps to be coupled with the medication reservoir 16 of these embodiments should preferably comprise a barcode label reader as well as a wireless memory reader like an RFID/NFC reader. However, it is also conceivable in principle to use in conjunction with the medication reservoir 16 according to the second to fourth preferred embodiments an infusion pump which is only provided with either a barcode reader or a wireless memory reader.

Further, it is conceivable in principle, that with the medication reservoir 16 according to the second and third embodiments of the FIGS. 4 and 5 the plate 28 is not provided with a barcode label or is even completely omitted, and that with the medication reservoir 16 of the fourth preferred embodiment of FIG. 6 the body 38 is completely omitted.

Figures 2, 7:
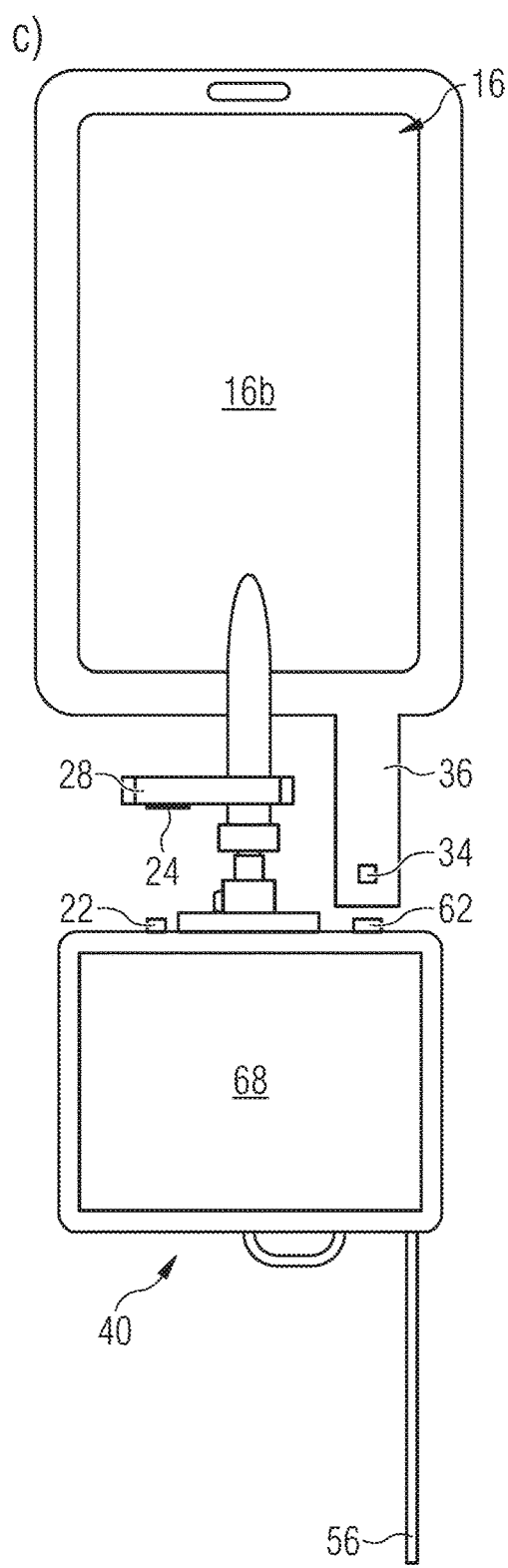
FIG. 7 shows a front view (a), a side view (b) and rear view (c) of an arrangement of an infusion pump according to a second preferred embodiment and the medication reservoir according to the third preferred embodiment of FIG. 5.

FIG. 7 shows an assembly or arrangement of an infusion pump 40 according to a second preferred embodiment with the medication reservoir 16 according to the third preferred embodiment of FIG. 5. As shown in FIG. 7a, the infusion pump 40 comprises—similar to the infusion pump 2 according to the first preferred embodiment of FIG. 1—as a first part a pump cartridge 42 and as a second part a pump module 44 which can also be called a pump controller. The pump cartridge 42 includes a pumping mechanism which is schematically shown in FIG. 7a and designated by the designating number "42a". The pump module 44 includes a motor (not shown) for driving the pump mechanism 42a. At the pump module 44 releasably attached is not only the pump cartridge 42 but also a drip chamber 46. The drip chamber 46 comprises an inlet port 48 which is configured as a spike in this embodiment and adapted to be coupled to the connector 26b of the medication reservoir 26 and, hence, in this embodiment defines the inlet port of the infusion pump 40. Besides the drip chamber 46 there are provided two ultrasound detectors wherein the upstream sensor 50 detects drops of the medication fluid so as to verify a correct performance of the infusion pump 40 and the downstream sensor 52 detects the level of the medication fluid within the drip chamber 46 and gives an alarm in case of detection of low level of the medication fluid. The drip chamber 46 is connected through a downstream tube 54 to the pump cartridge 42 which again is coupled to a downstream infusion line 56. As further shown in FIG. 7a, the drip chamber 46 is attached to the pump module 44 by snap fitting and drip chamber flaps up-stop means 60 at the upper end close to its inlet port 48. So, when the infusion pump 40 is connected to the medication reservoir 16, the drip chamber 46 hangs from the connector 26b of the medication reservoir 16 with which the inlet port 48 of the drip chamber 46 is coupled. Since the drip chamber 46 is attached by the snap fitting means 60 to the pump module 44, the pump module 44 and, hence, the whole infusion pump 40 is supported by the drip chamber 46.

In order to read the barcode label 24 at the underside or bottom of the plate 28, the pump module 44 is provided with the barcode reader 22 in a similar manner as the infusion pump 2 according to the first preferred embodiment so that regarding arrangement and configuration of the barcode reader 22 reference is made to the description of the first preferred embodiment of the infusion pump 2. Further, in order to also be able to read the RFID/NFC chip or label 34, the infusion pump 40 is also provided with a wireless memory reader which in the embodiment shown in FIG. 7 is configured as an RFID/NFC reader 62.

The pump module 44 comprises at its front side defining the front side 40a of the infusion pump 40 a display 64 and buttons 66 in a similar manner as the display 8 and the buttons 12 of the infusion pump 2 according to the first preferred embodiment of FIG. 1, wherein the buttons 66 have functions like purge, start/stop and on/off. In the embodiment of FIG. 7, the display 64 is a small display which is of black and white LCD technology and always switched on for showing critical information, but with backlight lighting only when needed so as to consume rather small amount of energy. In addition to this small display 64, the infusion pump 40 according to this embodiment further comprises at its back or rear side a large color touch display 68 which is advantageous for helping complex programming and interconnected services. This display 68 is preferably of plastic OLED flexible technology and therefore very thin and light-weight for a device hanging from the outlet port 26 of the medication reservoir. The display 68 can be covered by very thin glass of flexible glass technology as known in the art and able to prevent scratches without breaking. The display 68 turns on only for complex programming and IT networking tasks, and remains off most of the time for sake of large battery autonomy since the small display 64 at the front side of the pump module 44 consumes much less and, as already mentioned, is displaying the most critical information all the time.

Since with medication reservoirs 16 according to the second to fourth preferred embodiments as shown in the FIGS. 4 to 6 the barcode label 24 and the RFID/NFC label or chip 34 are arranged adjacent to the outlet port 26 and in particular on either side of the outlet port 26, the barcode reader 22 and the RFID/NFC reader 62 are positioned adjacent to the inlet port 48 and in particular on either side of the inlet port 48 on the top or the upper end face 40c of the infusion pump 40 as shown in FIG. 7. Of course, the barcode reader 22 is aligned in accordance with the barcode label 24 so as to be able to read it in a reliable manner, and the RFID/NFC reader 62 is positioned in an appropriate short distance from the RFID/NFC label 34 so as to be able to read it.

Hanging of the infusion pump 40 from the medication reservoir 16 is achieved because of its small size, so that it is hand held easily, and its weight is as low as 100 g having huge battery autonomy for a week of infusions or 7 liters of volume infused being fully ambulatory. While it is so ambulatory, its functions are fully bedside, with 1500 ml/h maximum infusion rate and adapted to complex "smart pump" programming using drug libraries and wireless communication and interoperability hospital infusion automation integration. Additionally the infusion pump 40 has dual processor safety, dual batteries and buzzers for full critical care and standard IEC60601-2-24 Edition III compliance. The infusion pump 40 is hanging from the spike 48 of the drip chamber 46 centrally embedded in pump housing preferably and has means to keep hanging like friction from the spike or further retention by means of a grip over tubing (not shown), or a connector to the tube (connector on both the tube 26a of the outlet port 26 of medication reservoir 16 and the upper inlet of drip chamber 46). For example a clip from the body of the infusion pump 40 that grips the tube 26a surrounding the spike 48 just above the connector 26b very close to the infusion pump 40 itself (not shown). The said clip can be snap gripping by placement, and released by single hand action which releases all this grip from reservoir and the drip chamber 46 and the pump cartridge 42 from the pump module 44. The medication reservoir 16 comprises the connector 26b (instead of a spike-tube connection) that can hang the weight of the pump 40 securely, and drip chamber 46 has also the appropriate connector too; so the connector 26b hangs the drip chamber 46, and the drip chamber 46 snap-fitted at the front side of the pump module 44 with the up-stop means 60 hangs the pump. The spike/tube specifications of the standard being for 1.5 Kg hanging force can withstand the weight of a pump of approx. 100 g. The said connector replacing a spike is standardized according to the application, as there are standards for luer connectors for intravenous, connectors for regional analgesia neuraxial NRFit, and connectors for enteral feeding in order to prevent accidental use of medications prepared for one application to another like enteral feeding delivered intravenously.

FIG. 8 shows the assembly or arrangement according to the embodiment of FIG. 7 which, however, is modified so as to be used in a piggy-back infusion configuration. In a piggy-back infusion configuration two medication reservoirs are used which are connected upstream to the infusion pump, wherein the infusion is carried out by one infusion pump from the one or the other medication reservoir depending on their height and, thus, the hydrostatic pressure of the medication. As shown in FIG. 8, the tube 54 connecting the drip chamber 46 with the pump cartridge 42 includes a stopcock valve 70 to which an upstream tube 72 is coupled coming from another medication reservoir (not shown here). Further, the pump module 44 comprises a stopcock valve position detector 74 which is arranged close to the stopcock valve 70 and is adapted to detect whether the stopcock valve 70 in a first position connects the drip chamber 46 to the pump cartridge 42 or in a second position connects the upstream tube 72 to the pump cartridge 42.

As mentioned above, piggyback infusions in today's practice have two reservoirs with so called primary and secondary medication upstream, connected to an Y connection, one reservoir higher than the other and so from static pressure difference, the higher is aspirated from the pump and the other is not; at some time the nurse changes the respective heights, and the other one is aspirated. Before change, the pump should be stopped and protocol changed to the other medication; it is this pump protocol change that sometimes is neglected and the pump starts with older protocol that may injure the patient.

Figure 12:
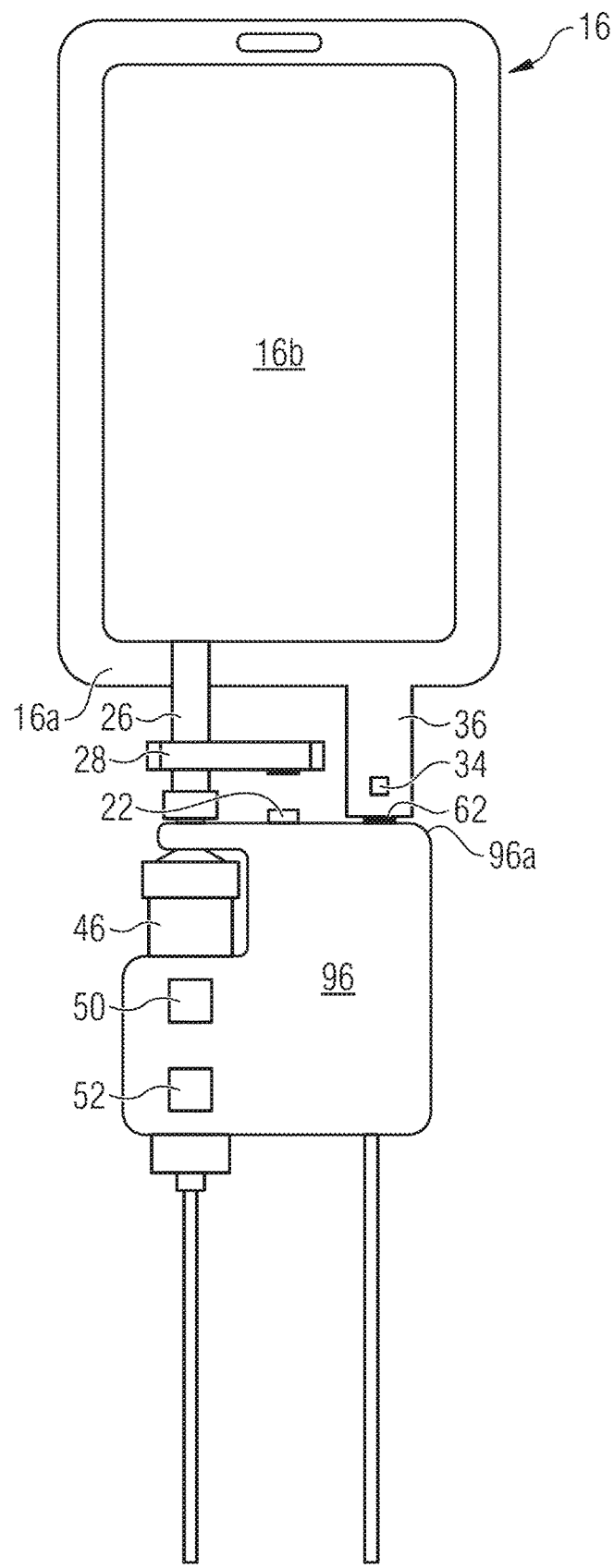
FIG. 12 an arrangement of the medication reservoir according to the fourth preferred embodiment of FIG. 6, an infusion pump module and a drip chamber loaded on the infusion pump.

100% medication error prevention with barcode/RFID in piggyback infusions is achieved with the above automatic reading barcode or RFID solution on primary medication directly in vicinity to the infusion pump 40 and secondary medication by the upstream tube 72 through the stopcock valve 70. So a nurse scans the barcode or RFID on both medications, plugs one direct on cartridge direct connection spike or connector so that the infusion pump 40 reads directly the barcode 24 in horizontal position with the barcode reader 22 and RFID with the RFID/NFC reader 62 as described above, and secondary medication is connected to a normal spike or a drip chamber with spike and is infused when the stopcock valve 70 is turned. The 100% safety is achieved because the infusion pump 40 knows the position of the valve 70 by means of the stopcock valve position reading detector 74 and from which of the two medications is infusing anytime because one directly read is associated with one valve position (direct), and assumes that the other (indirect) is associated with the other medication scanned but not able to be read again. In this arrangement the nurse does not need to change the respective height of the reservoirs but just the stopcock valve 70 so that the infusion pump 40 switches automatically infusion protocol to the correct medication preventing errors. The stopcock valve 70 can be placed on top or bottom of the drip chamber 46 closer to the pump, wherein in first case drugs are mixed in the drip chamber 46 and the infusion pump 40 has to be instructed what to do for few milliliters, and in second case not; both cases can have the stopcock position detector 74 in the pump, as an optic or magnetic or other type of sensor. Alternatively, the second medication reservoir at the end of the upstream tube 72 may have a device as shown in FIG. 12 where a flow sensor or an active valve is associated with a barcode reader 22 or a RFID/NFC reader 62 for best error prevention.

FIG. 9 shows an assembly or arrangement of medication reservoir, drip chamber and infusion pump which differs from the assemblies or arrangements of the FIGS. 7 and 8 in that as infusion pump the miniature infusion pump 2 according to the first preferred embodiment of FIG. 1 is used and the drip chamber 46 is positioned above the infusion pump 2 and below the medication reservoir 16 when the whole arrangement is in an operating position as shown in FIG. 9. The arrangement of the drip chamber 46 between the medication reservoir 16 and the infusion pump 2 results in a prolongation of the distance between the lower edge 16a of the medication reservoir 16 and the upper end face 2c of the infusion pump 2. Different from the first preferred embodiment shown in FIG. 1, but similar to the embodiments of FIGS. 7 and 8, the infusion pump 2 is provided in addition to the barcode reader 22 with the RFID/NFC reader 62 as wireless memory reader wherein both the barcode reader 22 and the RFID/NFC reader 62 are arranged on the upper end face 2c of the infusion pump 2. As already mentioned in conjunction with the description of the first preferred embodiment, the barcode reader 22 is provided with a light emitting diode LED or such a LED is arranged adjacent to the barcode reader 22 in order to illuminate the barcode label 24. Whereas the LED is not depicted here, FIG. 9b schematically shows the light beam 22b emitted from such a LED. The arrangement of FIG. 9 further differs from the arrangements of the FIGS. 7 and 8 in that the RFID/NFC label or chip 34 is not provided at the flap 36, but at the lower end of an extension 80 which is attached with its upper end to the flap 36. Due to the provision of such an extension 80 it is assured that the RFID/NFC label or chip 34 remains positioned adjacent to the RFID/NFC reader 62 within the required safe distance therefrom as shown in FIG. 9a.

Figure 10:
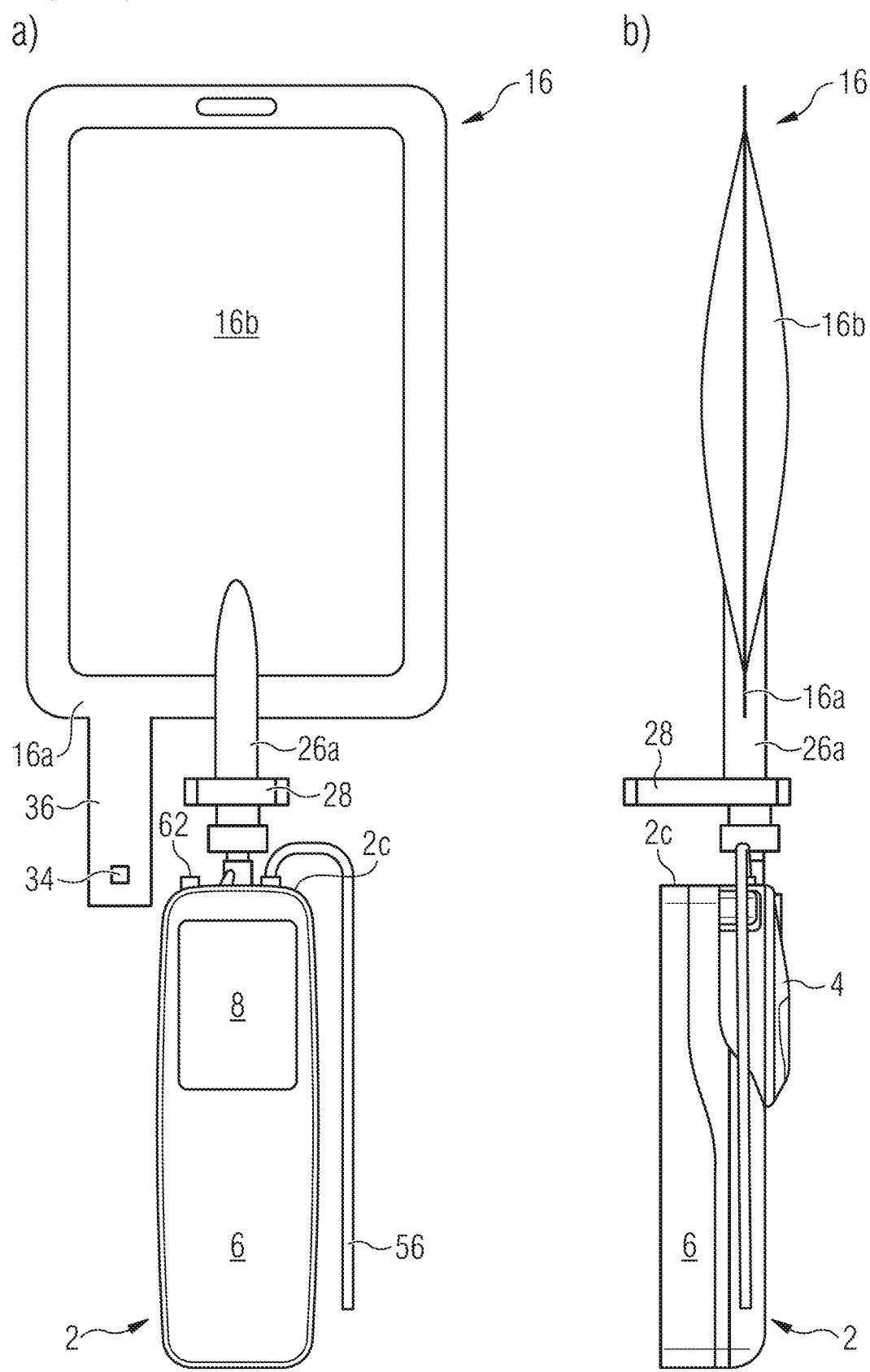
FIG. 10 shows a front view (a) and a side view (b) of an arrangement of the medication reservoir according to the third preferred embodiment of FIG. 5 and an infusion pump according to a third modification of the first embodiment of FIG. 1.

FIG. 10 shows an assembly or arrangement of the medication reservoir 16 and the infusion pump 2 according to a further embodiment which differs from the arrangement of FIG. 9 in that the infusion pump 2 is directly coupled so that the distance between the upper end face 2c of the infusion pump 2 on the one hand and the plate 28 and the lower edge 16a of the medication reservoir 16 and the tongue 36 with the RFID/NFC label or chip 34 on the other hand is about as short as in the arrangements of the FIGS. 7 and 8 and, hence, the provision of an extension 80 as in the embodiment of FIG. 9 is not necessary.

The present invention provides a novel way to label medication reservoirs, so that label is always readable from a barcode and/or RFID reader of an infusion system from start to end of an infusion and warn or alarm in case of medication change without any protocol change or check.

For doing so, the label may be printed on or self-adhesive bonded to an extension of the border sealing that can bend from vertical to horizontal as an "L" i.e. by 90 degrees showing barcode at its bottom and securely fasten to this position by any type of fastening known in the art (not shown) or as the strip 38 folded as a Delta and adhesive bonded on top showing downwards the barcode label 24 according to the fourth embodiment of medication reservoir 16 as shown in FIG. 6. The position of the label is such that its distance from the reader is nominal. So it can be on the border as a Δ extension below, or as a horizontal plastic clip or plate 28 fastened at the tube 26a of the outlet port 26 of the mediation reservoir 16 e.g. according to the second and third embodiments of FIGS. 4 and 5 or on the reservoir face. The label can be add-on or printed after filling for compounding, or permanent fixture for pharmaceutical prefilled medications. This type of pharmaceutical labeling for secure infusions makes the present invention a "drug delivery" implementation when associated with infusion system devices that respond to medication error prevention needs of the busy hospitals of today as a total solution.

The said infusion safe system devices are an association of an ID reader such as a barcode or RFID or both, to one of the following: a flow sensor, a flow enabler (active valve) or an infusion pump module or whole pump. ID reader can be also an electrical (parallel bits of information) or electronic (serial bits of information) contact device (FIG. 12).

In case of pump system use without lower barcode labels but conventional ones on the reservoir wall, the nurse at point of care connects the infusion set into the medication reservoir and primes it by gravity, points the pump towards patient's ID (bar-code or RFID) and reads it, then towards the medication reservoir and also reads it in case it reads bar-code, and then connects the pump on infusion set cartridge, then verifies protocol and 5R compliance. In this case, 100% safety is not achieved since while it is much better than conventional pumps of today attached on pole and having long upstream tubing, because still it is difficult but possible to scan the next reservoir instead of the just above pump reservoir on which it is to be connected.

The barcode and RFID/NFC labels are automatically read at setup, at start of infusion and at time intervals during infusion. Since the barcode reader 22 resides on top of the infusion pump 40 and the infusion pump 40 is also in line with the drip chamber 46 and so in line to the label just above drip chamber in particular in both preferred embodiments of FIGS. 7 and 9 as described above, in case of reservoir balancing on pole, alignment of label-tube-drip chamber-pump-barcode reader is assured and so reading is always possible and secure; it is not preferred to read label all time just for power consumption reasons except when the infusion pump 40 has wired or wireless power connection.

Medication delivery Safety is so absolutely 100% guaranteed in case of any of RFID/NFC or bar code reading. Namely, 100% safety is guaranteed in the present invention for the first time in the art, with barcode reading at start and eventually during infusion, so that the infusion pump 40 knows which reservoir or medication is being infused all the time so any accidental change will be discovered and alarm will be generated. For this 100% medication error prevention the barcode label 24 on reservoir 16 is at specific reading distance from just below pump as shown in FIG. 7 and FIG. 9 so that the barcode shows downwards so to be read from the pump's reader regularly.

It is a practice to get a medication reservoir of 50 to 100 ml with just a solution of saline or dextrose and add drugs from vials. The present invention helps pharmacy automation with means to print the recipe on a barcode 24 and attach it to the triangle shaped label plate 38 as shown in FIG. 6 or the horizontal plate 28 (cf. FIGS. 4, 5 and 7 to 10) fixed at the tube 26a of the medication reservoir 16 that will be spiked from the pump's infusion set at a specific distance range. A barcode or QR label is printed or adhesive bonded on the plate 28 as shown in the FIGS. 4, 5 and 7 to 10 wherein a safe reading distance is taken into consideration; in case of a serial drip chamber-pump arrangement of FIG. 9 the reading distance is about 10 cm achievable easily from a camera based barcode reader 22. The corners of the plate 28 at the tube 26a of the medication reservoir 16 are round and it may have a larger border to prevent damage of the reservoir sterile packaging.

Nurses when in a hurry today stop a pump, change the reservoir and forget to change protocol and restart the pump programmed for the former medication; with the present invention, since the pump automatically reads the nearby and accessible barcode or RFID every time before start or restart of infusion, this common error is eliminated sine an alarm will appear on medication error (wrong medication) detected.

Figure 11:
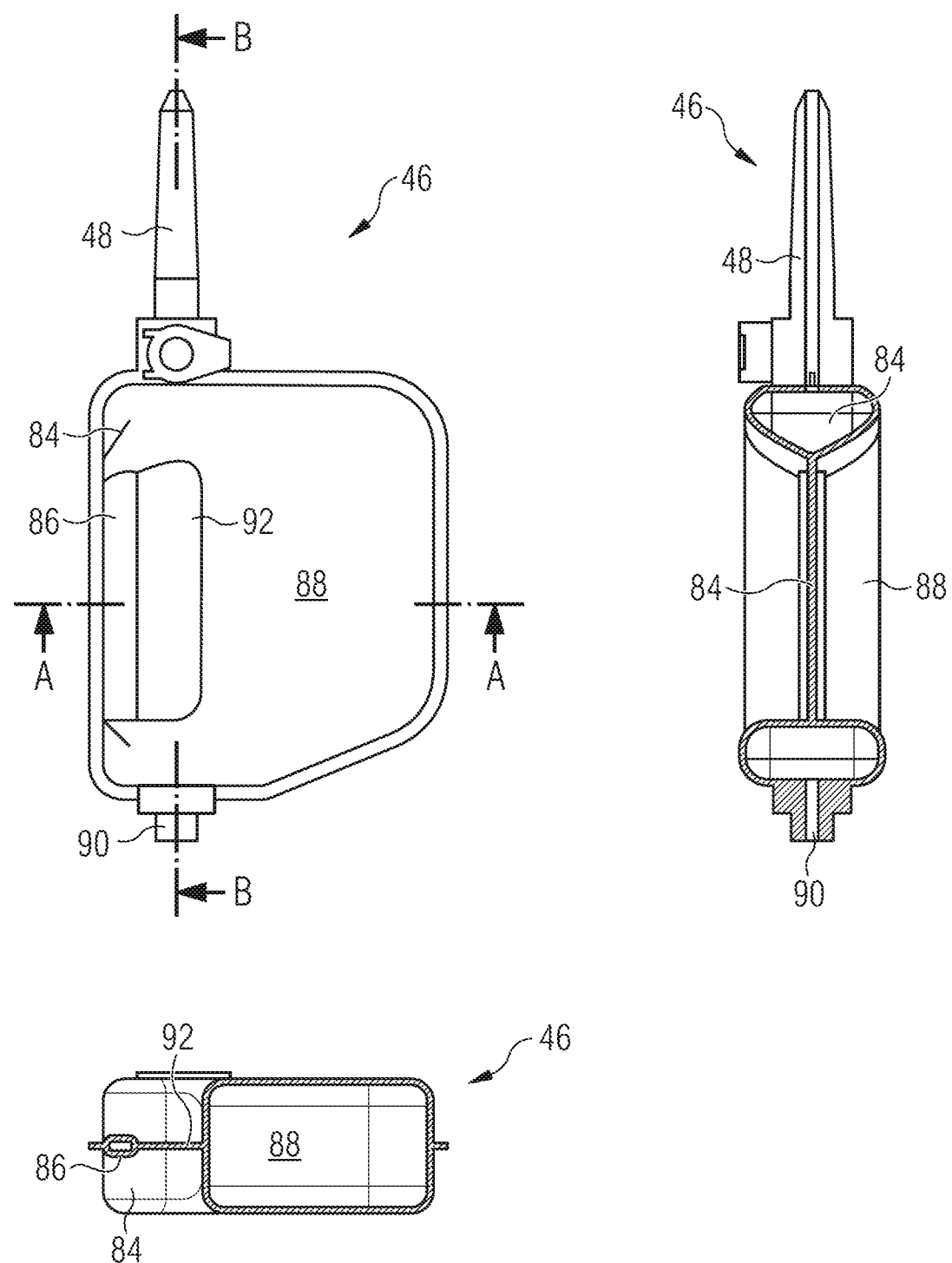
FIG. 11 shows a partly sectioned front view of a drip chamber according to a preferred embodiment (a), a sectional view through the drip chamber along the lines B-B in FIG. 11a (b) and sectional view through the drip chamber along the lines A-A in FIG. 11a (c)

FIG. 11 shows the drip chamber 46 according to a preferred embodiment in greater detail. The drip chamber 46 is provided with the inlet port 48 which is adapted to be connected to the outlet port 26 of the medication reservoir 16 as already shown in the FIGS. 7 to 9. As to be seen from the FIGS. 11a and b, the inlet port 48 of the drip chamber 46 is configured as a spike; however, the inlet port 48 may also have a different construction and for example be configured as a connector. The drip chamber 46 comprises a drop collecting portion 84 whose inlet is in fluid communication with the inlet port 48 of the drip chamber 46. As shown in FIG. 11b, the drop collecting portion 84 has an essentially V-shaped profile in the illustrated embodiment. FIG. 11 shows the drip chamber 46 in an operating position in which the drop collecting portion 84 is arranged below the inlet port 48. The drip chamber 46 according to the illustrated embodiment further includes a narrow channel 86 which is positioned below the drop collecting portion 84 and comprises an inlet being in fluid communication with an outlet of the drop collecting portion 84. As it becomes clear from the FIGS. 11b and c, the cross-sectional area of the channel 86 is smaller than the cross-sectional area of the drop collecting portion. Further, the drip chamber 46 includes a chamber portion 88 with which an outlet at the lower end of the channel 86 is in fluid communication. As shown in FIG. 11, the cross-sectional area and the volume of the chamber portion 88 are greater than those of the drop collecting portion 84 and the chamber 86. The drip chamber 46 further comprises a particles filter at the bottom (not shown) and an outlet port 90 which is in fluid communication with the chamber portion 88 and adapted to be connected to an inlet port of an infusion pump.

The drip chamber 46 comprises a casing which consists of two halves made of semi-soft plastic. For configuration of the drip chamber 46, the two halves of the casing are bonded together not only along their edges to form inter alia the chamber portion 88, but also along a contact line 92 in order to create the channel 86 which is separated by the contact line 92 from the chamber portion 88. The sensors 50, 52 as shown in the FIGS. 7 and 8 and described above in conjunction with the embodiment of FIG. 7 are to be arranged at the body of the infusion pump 40 and in particular the pump module 44 (cf. FIGS. 7 and 8) beside the channel 86.

It is known in the art that a drop from a drip chamber can be detected by optic means. In this preferred embodiment, it is provided the narrow channel 86 wherein a drop is sensed by an ultrasound air-in-line detector having much more reliable results. It is a nurse burden to look at the drip chamber drops after programming to assure correct infusion set placement, whereas the present invention has the pump checking correct drops per minute flow.

In this drip chamber 46 air is coming from the side up, and the drop collecting portion 84 on top narrowing to the channel 86 guides a drop into this narrow channel 86 so that it becomes a cylindrical fluid shape followed by air when it comes down and in contact with the fluid level below within the chamber portion 88.

The air stop feature is provided by a fluid level detector placed on the infusion pump 40 near the bottom of the drip chamber 46, using AIL ultrasound technique, optic, or other technologies known in the art. By doing so, the nurse is alarmed when the liquid level in the drip chamber 46 is low (medication is depleted), so that she presses the preferably semi-soft surface of the drip chamber 46 and air is pulsed back into the newly replaced reservoir since peristaltic mechanism on the other end blocks the path towards the patient, and then medication is aspirated to a preferred level in the drip chamber 46 when hand pressure on it is released. This air expulsion and liquid level restoring into the drip chamber 46 is very beneficial to nurse's work although the infusion pump 40 has Air-In-Line detector downstream which alarms then rarely.

The level detector software is using digital filtering techniques to filter out sudden level changes from a balancing reservoir during transportation or use. Furthermore, the pump preferably has a tilt sensor that senses if pump/drip chamber is not within +/−45 degrees vertical position.

The level detection is preferable from the prior art hydrophilic membrane since this membrane is not good for all infusions some needing larger filter mesh or filter area, and this prior art technology can delay alarm until pump senses upstream low pressure.

FIG. 12 shows an assembly or arrangement of a medication reservoir 16 according to the third preferred embodiment of FIG. 5 and an infusion pump controller 96 which is used for a plurality of upstream connected infusion pump modules (not shown) or alternatively for a conventional pole-mounted bedside multi-pump with a flow sensor or active valve modules. Similar to the infusion pump 40 of FIG. 7, the pump controller 96 includes the drip chamber 46 and the sensors 50, 52 as already described above and is also provided with the barcode reader 22 and the RFID/NFC reader 62 on its upper end face 26a pointing to the medication reservoir 16.

Each pump, flow sensor or active valve module has associated an ID reading device such as RFID, Barcode or contact electrical/electronic, and connection with a pump or pump controller. In this case, flow sensor and level detector are on the module that can also have also an active valve or infusion pump module. ID reading device together an infusion or flow sensing/enabling device at same module, assures 100% safety of infusing from the correct reservoir and it is up to preparation automation to assure that each labeling medication is put in correct labeled reservoir. Namely, an infusion pump knows directly to which label is attached and infusing.

A flow sensor senses when a flow starts and pump alarms if flow and start are not synchronized therefore there is an erroneous connection (wrong medication); flow sensor has also level detector at bottom as all these three cases (pump, flow, valve) do. An active valve is closed when infusion starts, and so upstream block from pressure drop is detected, assuring that pump is connected to the correct medication reservoir, and then valve opens for infusion to start. Such a configuration is valuable for upgrading standard LVP infusion pumps or for achieving a total safety with piggyback infusions placed at the end of the upstream tube 72 connected to a distant medication reservoir according to the arrangement of FIG. 8.

FIG. 13 shows a rack configuration comprising an inclined plate 100 which is attached to a vertical pole 102 and supports a plurality of assemblies or arrangements each consisting of a medication reservoir and an infusion pump. In the embodiment shown in FIG. 13, the arrangements of a medication reservoir 16 and an infusion pump 2 according to the embodiment of FIG. 10 are provided. As shown in FIGS. 13b and c, each arrangement of medication reservoir 16 and infusion pump 2 are supported by a horizontal pivot 104 at the plate 100. As shown in FIG. 13a, the arrangements of medication reservoir 16 and infusion pump 2 and, hence, the medication reservoirs 16 are disposed side by side so that air contained in the medication reservoirs 16 can still go up. In order to achieve this effect, the inclined plate 100 is aligned under an angle of preferably 20 to 45°. The rack configuration as shown in FIG. 13 is advantageous for mini-bags replacing syringes or syringe pump stacks in operating rooms, wherein each infusion pump 2 is also inclined due to a direct connection to the associated medication reservoir 16. A bigger medication reservoir may hang vertically at the same level or at a higher position on the pole 102 along with an upstream tube connection, which all is not shown here. An easy pump handling is achieved by the horizontal pivot 104 which is provided at each pump location on the inclined plate 100.

FIG. 14 shows a modification of the embodiment of FIG. 13 wherein each of the assemblies or arrangements of medication reservoir 16 and infusion pump 2 (FIG. 14a exemplarily shows only one of a plurality of such assemblies or arrangements) is supported by a clamp 106 which is hinged at the inclined plate 100 about the horizontal pivot 104. So, each assembly or arrangement of medication reservoir 16 and infusion pump 2 can rotate over the horizontal axis of the horizontal pivot 104, allowing a positioning at an inclined or a vertical reservoir fluid connection and also an easy handling of the infusion pump 2 itself for programming, infusion control or replacement of the pump cartridge 4 (FIG. 1) at its back.

The invention claimed is:

1. An infusion system including an infusion pump, wherein the infusion pump comprises:
a display screen,
a barcode reader adapted to read a barcode provided at a medication reservoir, wherein the barcode reader is positioned on the infusion pump such that (a) when the infusion pump is connected to the medication reservoir, a reading direction of the barcode reader is oriented towards the barcode provided at the medication reservoir, and (b) the reading direction of the barcode reader is oriented away from the display screen at an angle greater than 90° to a plane of the display screen; and
an inlet port adapted to be coupled directly to an outlet port of the medication reservoir, wherein the barcode reader is arranged on the infusion pump such that the reading direction of the barcode reader is oriented in a direction of coupling of the inlet port of the infusion pump with the outlet port of the medication reservoir.

2. The infusion system according to claim 1, wherein the barcode reader is arranged such that it's the reading direction of the barcode reader is oriented parallel to the plane of the display screen.

3. The infusion system according to claim 1, wherein the barcode reader is positioned above the display screen when the infusion pump is in an operating position.

4. The infusion system according to claim 1, wherein the infusion pump comprises a first surface portion and a second surface portion, wherein the display screen is provided at the first surface portion and the barcode reader is provided at the second surface portion, and wherein the second surface portion is arranged at an angle of about 90°, to the first surface portion.

5. The infusion system according to claim 4, wherein the second surface portion forms an end face of the infusion pump.

6. The infusion system according to claim 4, wherein the infusion pump includes an inlet port provided at the second surface portion.

7. The infusion system according to claim 1, wherein the barcode reader is positioned beside the inlet port of the infusion pump.

8. The infusion system according to claim 1, wherein the infusion pump further comprises a first part which includes a pump mechanism, and a second part which includes a motor for driving the pump mechanism of the first part, and wherein (i) the first part is releasably attachable to the second part, (ii) the first part is provided with the inlet port, and (iii) the second part is provided with the barcode reader.

* * * * *

UNITED STATES PATENT AND TRADEMARK OFFICE
CERTIFICATE OF CORRECTION

PATENT NO. : 10,940,261 B2  
APPLICATION NO. : 15/485766  
DATED : March 9, 2021  
INVENTOR(S) : Achilleas Tsoukalis Page 1 of 1

It is certified that error appears in the above-identified patent and that said Letters Patent is hereby corrected as shown below:

In the Claims

Column 20, Line 36, in Claim 2, delete "it's"

Signed and Sealed this  
Fourth Day of May, 2021

Drew Hirshfeld  
*Performing the Functions and Duties of the*  
*Under Secretary of Commerce for Intellectual Property and*  
*Director of the United States Patent and Trademark Office*